United States Patent
McAfee et al.

(10) Patent No.: US 11,612,436 B2
(45) Date of Patent: Mar. 28, 2023

(54) SYSTEMS, METHODS, AND DEVICES FOR DEVELOPING PATIENT-SPECIFIC MEDICAL TREATMENTS, OPERATIONS, AND PROCEDURES

(71) Applicant: Medicrea International, Rillieux-la-Pape (FR)

(72) Inventors: Paul C. McAfee, Sparks, MD (US); Elliott Dobbs, Palm Coast, FL (US); Thomas Mosnier, Rochetaillée sur Saône (FR)

(73) Assignee: MEDICREA INTERNATIONAL

( * ) Notice: Subject to any disclaimer, the term of this patent is extended or adjusted under 35 U.S.C. 154(b) by 896 days.

(21) Appl. No.: 16/404,276

(22) Filed: May 6, 2019

(65) Prior Publication Data
US 2019/0380782 A1 Dec. 19, 2019

Related U.S. Application Data

(63) Continuation-in-part of application No. PCT/FR2017/053506, filed on Dec. 12, 2017.
(Continued)

(51) Int. Cl.
*A61B 34/10* (2016.01)
*A61B 90/00* (2016.01)
(Continued)

(52) U.S. Cl.
CPC .............. *A61B 34/10* (2016.02); *A61B 17/70* (2013.01); *A61B 90/39* (2016.02); *A61B 2017/568* (2013.01); *A61B 2034/102* (2016.02); *A61B 2034/105* (2016.02); *A61B 2034/108* (2016.02); *G06T 2207/30012* (2013.01)

(58) Field of Classification Search
CPC .............. A61B 34/10; A61B 2034/102; A61B 2034/108; A61B 2017/568
See application file for complete search history.

(56) References Cited

U.S. PATENT DOCUMENTS

| 4,382,438 A | 5/1983 | Jacobs |
| 5,006,984 A | 4/1991 | Steele |

(Continued)

FOREIGN PATENT DOCUMENTS

| AU | 2015258176 | 12/2015 |
| AU | 2015202416 | 3/2017 |

(Continued)

OTHER PUBLICATIONS

US 9,451,972 B2, 09/2016, Lang et al. (withdrawn)
(Continued)

*Primary Examiner* — Anu Ramana
(74) *Attorney, Agent, or Firm* — Fox Rothschild LLP

(57) ABSTRACT

Certain systems, methods, and devices described herein are configured to dynamically model a patient area for surgery and/or other treatment, dynamically identify one or more features and/or characteristics thereon such as the length and/or elasticity of the posterior longitudinal ligament (PLL), dynamically allow modification of the model, dynamically limit and/or assist in modification of the model, and/or dynamically generate guidelines for generation of patient-specific implants and/or treatment kits for a specific patient.

16 Claims, 28 Drawing Sheets

Related U.S. Application Data

(60) Provisional application No. 62/777,906, filed on Dec. 11, 2018, provisional application No. 62/506,855, filed on May 16, 2017, provisional application No. 62/433,102, filed on Dec. 12, 2016.

(51) Int. Cl.
*A61B 17/70* (2006.01)
*A61B 17/56* (2006.01)

(56) References Cited

U.S. PATENT DOCUMENTS

| | | | |
|---|---|---|---|
| 5,163,440 A | 11/1992 | DeLuca et al. | |
| 5,209,752 A | 5/1993 | Ashman et al. | |
| 5,224,035 A | 6/1993 | Yamashita et al. | |
| 5,251,127 A | 10/1993 | Raab | |
| 5,291,901 A | 3/1994 | Graf | |
| 5,305,203 A | 4/1994 | Raab | |
| 5,312,405 A | 5/1994 | Korotko et al. | |
| 5,413,116 A | 5/1995 | Radke et al. | |
| 5,514,180 A | 5/1996 | Heggeness | |
| 5,667,506 A | 9/1997 | Sutterlin | |
| 5,748,767 A | 5/1998 | Raab | |
| 5,785,663 A | 7/1998 | Sarvazyan | |
| 6,015,409 A | 1/2000 | Jackson | |
| 6,213,958 B1 | 4/2001 | Winder | |
| 6,282,437 B1 | 8/2001 | Franck et al. | |
| 6,302,888 B1 | 10/2001 | Mellinger et al. | |
| 6,364,849 B1 | 4/2002 | Wilcox | |
| 6,385,475 B1 | 5/2002 | Cinquin et al. | |
| 6,409,684 B1 | 6/2002 | Wilk | |
| 6,443,953 B1 | 9/2002 | Perra et al. | |
| 6,499,488 B1 | 12/2002 | Hunter et al. | |
| 6,565,519 B2 | 5/2003 | Benesh | |
| 6,585,666 B2 | 7/2003 | Suh et al. | |
| 6,701,174 B1 * | 3/2004 | Krause | G06T 17/10 600/407 |
| 6,711,432 B1 | 3/2004 | Krause et al. | |
| 6,715,213 B2 | 4/2004 | Richter | |
| 6,716,213 B2 | 4/2004 | Shitoto | |
| 6,746,449 B2 | 6/2004 | Jones et al. | |
| 6,786,930 B2 | 9/2004 | Biscup | |
| 7,066,938 B2 | 6/2006 | Slivka et al. | |
| 7,338,526 B2 | 3/2008 | Steinberg et al. | |
| 7,509,183 B2 | 3/2009 | Lin | |
| 7,534,263 B2 | 5/2009 | Burduiis | |
| 7,542,791 B2 | 6/2009 | Mire et al. | |
| 7,570,791 B2 | 8/2009 | Frank et al. | |
| 7,606,613 B2 | 10/2009 | Simon et al. | |
| 7,611,522 B2 | 11/2009 | Gorek | |
| 7,618,451 B2 | 11/2009 | Fitz et al. | |
| 7,634,119 B2 | 12/2009 | Tsougarakis et al. | |
| 7,635,367 B2 | 12/2009 | Groiso | |
| 7,639,866 B2 | 12/2009 | Pomero et al. | |
| 7,660,623 B2 | 2/2010 | Hunter et al. | |
| 7,674,293 B2 | 3/2010 | Kuiper et al. | |
| 7,715,602 B2 | 5/2010 | Richard | |
| 7,763,054 B2 | 7/2010 | Clement et al. | |
| 7,824,413 B2 | 11/2010 | Varieur et al. | |
| 7,835,778 B2 | 11/2010 | Foley et al. | |
| 7,840,253 B2 | 11/2010 | Tremblay et al. | |
| 7,862,593 B2 | 1/2011 | Clement et al. | |
| 7,918,887 B2 | 4/2011 | Roche | |
| 7,953,471 B2 | 5/2011 | Clayton et al. | |
| 7,974,677 B2 | 7/2011 | Mire et al. | |
| 7,981,158 B2 | 7/2011 | Fitz et al. | |
| 7,996,061 B2 | 8/2011 | Mollard et al. | |
| 7,996,064 B2 | 8/2011 | Simon et al. | |
| 8,000,926 B2 | 8/2011 | Roche et al. | |
| 8,036,441 B2 | 10/2011 | Frank et al. | |
| 8,038,716 B2 | 10/2011 | Duggal et al. | |
| 8,046,050 B2 | 10/2011 | Govari et al. | |
| 8,066,708 B2 | 11/2011 | Lang et al. | |
| 8,077,950 B2 | 12/2011 | Tsougarakis et al. | |
| 8,083,778 B2 | 12/2011 | Clemet et al. | |
| 8,105,330 B2 | 1/2012 | Fitz et al. | |
| 8,142,842 B2 | 3/2012 | Nicholas et al. | |
| 8,196,825 B2 | 6/2012 | Turner et al. | |
| 8,211,109 B2 | 7/2012 | Groiso | |
| 8,211,153 B2 | 7/2012 | Shaolian et al. | |
| 8,234,097 B2 * | 7/2012 | Steines | A61F 2/3859 703/11 |
| 8,241,296 B2 | 8/2012 | Wasielewski | |
| 8,246,680 B2 | 8/2012 | Betz et al. | |
| 8,265,790 B2 | 9/2012 | Amiot et al. | |
| 8,270,253 B1 | 9/2012 | Roche et al. | |
| 8,275,594 B2 | 9/2012 | Lin et al. | |
| 8,308,772 B2 | 11/2012 | Clemet et al. | |
| 8,308,775 B2 | 11/2012 | Clement et al. | |
| 8,337,501 B2 | 12/2012 | Fitz et al. | |
| 8,357,111 B2 | 1/2013 | Caillouette et al. | |
| 8,357,166 B2 | 1/2013 | Aram et al. | |
| 8,372,075 B2 | 2/2013 | Groiso | |
| 8,377,073 B2 | 2/2013 | Wasielewski | |
| 8,394,142 B2 | 3/2013 | Berg et al. | |
| 8,398,681 B2 | 3/2013 | Augostino et al. | |
| 8,400,312 B2 | 3/2013 | Hotokebuchi et al. | |
| 8,414,592 B2 | 4/2013 | Quirno | |
| 8,442,621 B2 | 5/2013 | Gorek et al. | |
| 8,457,930 B2 | 6/2013 | Schroeder | |
| 8,465,527 B2 | 6/2013 | Clement | |
| 8,480,754 B2 * | 7/2013 | Bojarski | A61F 2/5046 623/20.14 |
| 8,494,805 B2 | 7/2013 | Roche et al. | |
| 8,506,632 B2 | 8/2013 | Ganem et al. | |
| 8,532,806 B1 | 9/2013 | Masson | |
| 8,535,337 B2 | 9/2013 | Chang et al. | |
| 8,549,888 B2 | 10/2013 | Isaacs | |
| 8,556,983 B2 | 10/2013 | Bojarski et al. | |
| 8,588,892 B2 | 11/2013 | Hladio et al. | |
| 8,636,776 B2 | 1/2014 | Rosenberg et al. | |
| 8,672,948 B2 | 3/2014 | Lemaitre | |
| 8,685,093 B2 | 4/2014 | Anderson et al. | |
| 8,690,888 B2 | 4/2014 | Stein et al. | |
| 8,705,829 B2 | 4/2014 | Frank et al. | |
| 8,718,820 B2 | 5/2014 | Amiot et al. | |
| 8,758,357 B2 | 6/2014 | Frey | |
| 8,775,133 B2 | 7/2014 | Schroeder | |
| 8,777,877 B2 | 7/2014 | Stein et al. | |
| 8,784,339 B2 | 7/2014 | Stein et al. | |
| 8,801,786 B2 | 8/2014 | Bernard et al. | |
| 8,814,877 B2 | 8/2014 | Wasielewski | |
| 8,814,915 B2 | 8/2014 | Hess et al. | |
| 8,852,237 B2 | 10/2014 | Kalfas et al. | |
| 8,855,389 B1 | 10/2014 | Hoffman et al. | |
| 8,864,764 B2 | 10/2014 | Groiso | |
| 8,870,889 B2 | 10/2014 | Frey | |
| 8,900,316 B2 | 12/2014 | Lenz | |
| 8,906,107 B2 * | 12/2014 | Bojarski | A61F 2/389 623/20.35 |
| 8,911,448 B2 | 12/2014 | Stein | |
| 8,926,673 B2 | 1/2015 | Clement et al. | |
| 8,926,706 B2 * | 1/2015 | Bojarski | A61B 17/157 623/20.35 |
| 8,945,133 B2 | 2/2015 | Stein et al. | |
| 8,956,416 B2 | 2/2015 | McCarthy | |
| 8,974,467 B2 | 3/2015 | Stone | |
| 8,983,813 B2 | 3/2015 | Miles et al. | |
| 8,998,962 B2 | 4/2015 | Birch | |
| 9,011,448 B2 | 4/2015 | Roche et al. | |
| 9,034,037 B2 | 5/2015 | Fiere et al. | |
| 9,039,772 B2 | 5/2015 | Park et al. | |
| 9,056,017 B2 | 6/2015 | Kotlus | |
| 9,066,701 B1 | 6/2015 | Finley et al. | |
| 9,066,734 B2 | 6/2015 | Schoenefeld et al. | |
| 9,078,755 B2 | 7/2015 | Mahfouz | |
| 9,101,492 B2 | 8/2015 | Mangione et al. | |
| 9,115,998 B2 | 8/2015 | Proulx et al. | |
| 9,119,572 B2 | 9/2015 | Gorek et al. | |
| 9,119,671 B2 | 9/2015 | Kast | |
| 9,125,680 B2 | 9/2015 | Kostrzewski et al. | |
| 9,144,440 B2 | 9/2015 | Aminian | |
| 9,144,470 B2 | 9/2015 | Proulx et al. | |

(56) References Cited

U.S. PATENT DOCUMENTS

| | | | |
|---|---|---|---|
| 9,168,153 B2 | 10/2015 | Bettenga | |
| 9,173,661 B2 | 11/2015 | Metzger et al. | |
| 9,180,015 B2 | 11/2015 | Fitz et al. | |
| 9,192,412 B2 | 11/2015 | Meyrat et al. | |
| 9,198,678 B2 | 12/2015 | Frey et al. | |
| 9,232,955 B2 | 1/2016 | Bonin, Jr. et al. | |
| 9,233,001 B2 | 1/2016 | Miles et al. | |
| 9,237,952 B2 | 1/2016 | Kurtz | |
| 9,248,023 B2 | 2/2016 | Ries et al. | |
| 9,250,620 B2 | 2/2016 | Kotlus | |
| 9,278,010 B2 | 3/2016 | Gibson et al. | |
| 9,283,048 B2 | 3/2016 | Kostrzewski et al. | |
| 9,289,221 B2 | 3/2016 | Gelaude et al. | |
| 9,289,270 B2 | 3/2016 | Gieien et al. | |
| 9,295,482 B2 | 3/2016 | Fitz et al. | |
| 9,295,497 B2 | 3/2016 | Schoenfeld et al. | |
| 9,295,561 B2 | 3/2016 | Ball et al. | |
| 9,301,768 B2 | 4/2016 | Buza et al. | |
| 9,308,050 B2 | 4/2016 | Kostrzewski et al. | |
| 9,308,091 B2 | 4/2016 | Lang | |
| 9,314,275 B2 | 4/2016 | Clement et al. | |
| 9,314,343 B2 | 4/2016 | Parisi et al. | |
| 9,320,547 B2 | 4/2016 | Augostino | |
| 9,320,604 B2 | 4/2016 | Miles et al. | |
| 9,320,620 B2 * | 4/2016 | Bojarski | A61B 17/157 |
| 9,326,780 B2 | 5/2016 | Wong et al. | |
| 9,339,277 B2 | 5/2016 | Jansen et al. | |
| 9,345,492 B2 | 5/2016 | Stein et al. | |
| 9,358,051 B2 | 6/2016 | Sournac et al. | |
| 9,358,130 B2 | 6/2016 | Livorsi et al. | |
| 9,358,136 B2 | 6/2016 | Stein et al. | |
| 9,364,370 B2 | 6/2016 | Kühnel | |
| 9,381,085 B2 | 7/2016 | Axelson et al. | |
| 9,387,015 B2 | 7/2016 | Taylor | |
| 9,392,953 B1 | 7/2016 | Gharib | |
| 9,393,052 B2 | 7/2016 | Berg et al. | |
| 9,398,962 B2 | 7/2016 | Steinberg | |
| 9,402,726 B2 | 8/2016 | Linderman et al. | |
| 9,408,615 B2 | 8/2016 | Fitz et al. | |
| 9,408,642 B2 | 8/2016 | Wong et al. | |
| 9,408,698 B2 | 8/2016 | Miles et al. | |
| 9,414,940 B2 | 8/2016 | Stein et al. | |
| 9,433,443 B2 | 9/2016 | Montello et al. | |
| 9,439,659 B2 | 9/2016 | Schoenefeld et al. | |
| 9,439,767 B2 | 9/2016 | Bojarski et al. | |
| 9,439,781 B2 | 9/2016 | Gibson | |
| 9,445,913 B2 | 9/2016 | Donner et al. | |
| 9,452,022 B2 | 9/2016 | McIntosh et al. | |
| 9,452,023 B2 | 9/2016 | Boillot et al. | |
| 9,452,050 B2 | 9/2016 | Miles et al. | |
| 9,452,064 B2 | 9/2016 | Trautwein et al. | |
| 9,468,436 B2 | 10/2016 | Groiso | |
| 9,468,502 B2 | 10/2016 | Wiebe et al. | |
| 9,491,415 B2 | 11/2016 | Deitz et al. | |
| 9,492,183 B2 | 11/2016 | Wilkinson et al. | |
| 9,495,483 B2 * | 11/2016 | Steines | A61F 2/3859 |
| 9,495,509 B2 | 11/2016 | Amiot et al. | |
| 9,498,260 B2 | 11/2016 | Funk et al. | |
| 9,504,502 B2 | 11/2016 | Kuiper et al. | |
| 9,510,771 B1 | 12/2016 | Finley et al. | |
| 9,510,864 B2 | 12/2016 | Devito | |
| 9,517,134 B2 | 12/2016 | Lang | |
| 9,517,143 B2 | 12/2016 | Prevost et al. | |
| 9,526,514 B2 | 12/2016 | Kelley et al. | |
| 9,532,730 B2 | 1/2017 | Wasielewski | |
| 9,539,031 B2 | 1/2017 | Fauth | |
| 9,539,116 B2 | 1/2017 | Claypool et al. | |
| 9,539,760 B2 | 1/2017 | Stahl et al. | |
| 9,547,897 B2 | 1/2017 | Parent et al. | |
| 9,549,782 B2 | 1/2017 | Park et al. | |
| 9,554,411 B1 | 1/2017 | Hall et al. | |
| 9,554,910 B2 | 1/2017 | Vanasse et al. | |
| 9,561,115 B2 | 2/2017 | Elahinia et al. | |
| 9,566,075 B2 | 2/2017 | Carroll | |
| 9,579,043 B2 | 2/2017 | Chien et al. | |
| 9,585,597 B2 | 3/2017 | McCaullet et al. | |
| 9,597,096 B2 | 3/2017 | Aghazadeh | |
| 9,597,156 B2 | 3/2017 | Amiot et al. | |
| 9,600,138 B2 * | 3/2017 | Thomas | G06T 7/0012 |
| 9,603,613 B2 | 3/2017 | Schoenefeld et al. | |
| 9,603,623 B2 | 3/2017 | Brooks et al. | |
| 9,603,711 B2 | 3/2017 | Bojarski et al. | |
| 9,610,086 B2 | 4/2017 | Park et al. | |
| 9,615,834 B2 | 4/2017 | Agmihotri et al. | |
| 9,622,712 B2 | 4/2017 | Munro et al. | |
| 9,629,723 B2 | 4/2017 | Parisi et al. | |
| 9,636,181 B2 | 5/2017 | Isaacs | |
| 9,642,633 B2 | 5/2017 | Frey et al. | |
| 9,649,170 B2 | 5/2017 | Park et al. | |
| 9,655,729 B2 | 5/2017 | Parisi et al. | |
| 9,662,214 B2 | 5/2017 | Li et al. | |
| 9,668,748 B2 | 6/2017 | McKinnon et al. | |
| 9,668,873 B2 | 6/2017 | Winslow | |
| 9,675,471 B2 | 6/2017 | Bojarski et al. | |
| 9,693,831 B2 | 7/2017 | Mosnier | |
| 9,715,563 B1 | 7/2017 | Schroeder | |
| 9,757,072 B1 | 9/2017 | Urbalejo | |
| 9,782,228 B2 | 10/2017 | Mosnier et al. | |
| 9,788,966 B2 | 10/2017 | Steinberg | |
| 9,827,109 B2 | 11/2017 | Steinberg | |
| 9,848,922 B2 | 12/2017 | Tohmeh et al. | |
| 9,968,408 B1 | 5/2018 | Casey et al. | |
| 9,987,048 B2 | 6/2018 | Mosnier et al. | |
| 9,993,177 B2 | 6/2018 | Chien et al. | |
| 10,010,426 B2 | 7/2018 | Kuiper et al. | |
| 10,045,824 B2 | 8/2018 | Mosnier et al. | |
| 10,052,135 B2 | 8/2018 | Berg et al. | |
| 10,064,743 B2 | 9/2018 | Funk et al. | |
| 10,098,671 B2 | 10/2018 | Augostino | |
| 10,188,480 B2 | 1/2019 | Scholl et al. | |
| 10,201,320 B2 | 2/2019 | Saget | |
| 10,219,865 B2 | 3/2019 | Jansen | |
| 10,314,657 B2 | 6/2019 | Mosnier et al. | |
| 10,318,655 B2 | 6/2019 | Mosnier | |
| 10,413,365 B1 | 9/2019 | Mosnier et al. | |
| 10,420,615 B1 | 9/2019 | Mosnier et al. | |
| 10,433,893 B1 | 10/2019 | Scholl et al. | |
| 10,433,912 B1 | 10/2019 | Mosnier et al. | |
| 10,433,913 B2 | 10/2019 | Mosnier et al. | |
| 10,441,363 B1 | 10/2019 | Mosnier et al. | |
| 10,456,211 B2 | 10/2019 | Mosnier et al. | |
| 10,463,433 B2 | 11/2019 | Turner et al. | |
| 2002/0035321 A1 | 3/2002 | Bucholz et al. | |
| 2002/0038118 A1 | 3/2002 | Shoham | |
| 2002/0045812 A1 | 4/2002 | Ben-Haim et al. | |
| 2002/0103432 A1 | 8/2002 | Kawchuk | |
| 2003/0191383 A1 | 10/2003 | Ben-Haim et al. | |
| 2003/0204189 A1 | 10/2003 | O'Neil et al. | |
| 2004/0120781 A1 | 6/2004 | Luca | |
| 2004/0143243 A1 | 7/2004 | Wahrburg | |
| 2004/0152972 A1 | 8/2004 | Hunter | |
| 2004/0167637 A1 | 8/2004 | Biscup | |
| 2004/0172020 A1 | 9/2004 | Beaurain et al. | |
| 2004/0215190 A1 | 10/2004 | Nguyen et al. | |
| 2004/0243148 A1 | 12/2004 | Wasuekewski | |
| 2004/0267279 A1 | 12/2004 | Casutt et al. | |
| 2005/0149050 A1 | 7/2005 | Stifter et al. | |
| 2005/0177239 A1 | 8/2005 | Steinberg | |
| 2005/0182320 A1 | 8/2005 | Stifter et al. | |
| 2005/0182454 A1 | 8/2005 | Kaula et al. | |
| 2005/0203531 A1 | 9/2005 | Lakin et al. | |
| 2005/0203532 A1 | 9/2005 | Ferguson et al. | |
| 2005/0262911 A1 | 12/2005 | Dankowicz et al. | |
| 2006/0015018 A1 | 1/2006 | Jutras et al. | |
| 2006/0015030 A1 | 1/2006 | Poulin et al. | |
| 2006/0069324 A1 | 3/2006 | Block et al. | |
| 2006/0074431 A1 | 4/2006 | Sutton et al. | |
| 2006/0136058 A1 | 6/2006 | Pietrzak | |
| 2006/0285991 A1 | 12/2006 | McKinley | |
| 2006/0287627 A1 | 12/2006 | Johnson | |
| 2007/0021682 A1 | 1/2007 | Gharib et al. | |
| 2007/0118243 A1 | 5/2007 | Schroeder et al. | |
| 2007/0225731 A1 | 9/2007 | Couture et al. | |
| 2008/0058945 A1 | 3/2008 | Hajaj et al. | |

(56) References Cited

U.S. PATENT DOCUMENTS

| | | |
|---|---|---|
| 2008/0108991 A1 | 5/2008 | von Jako |
| 2008/0177203 A1 | 7/2008 | von Jako |
| 2008/0255575 A1 | 10/2008 | Justis et al. |
| 2009/0024164 A1 | 1/2009 | Neubardt |
| 2009/0076615 A1 | 3/2009 | Duggal et al. |
| 2009/0157083 A1 | 6/2009 | Park et al. |
| 2009/0194206 A1 | 8/2009 | Jeon et al. |
| 2009/0204159 A1 | 8/2009 | Justis et al. |
| 2009/0248080 A1 | 8/2009 | Justis et al. |
| 2009/0249851 A1 | 10/2009 | Isaacs |
| 2009/0254326 A1 | 10/2009 | Isaacs |
| 2010/0042157 A1 | 2/2010 | Trieu |
| 2010/0100011 A1 | 4/2010 | Roche |
| 2010/0191071 A1* | 7/2010 | Anderson .............. G16H 50/50 703/11 |
| 2010/0191088 A1* | 7/2010 | Anderson .............. A61B 34/20 606/300 |
| 2010/0217270 A1 | 8/2010 | Polinski et al. |
| 2010/0217336 A1 | 8/2010 | Crawford et al. |
| 2011/0004309 A9 | 3/2011 | Bojarski et al. |
| 2011/0071802 A1 | 3/2011 | Bojarski et al. |
| 2011/0118740 A1 | 5/2011 | Rabiner et al. |
| 2011/0172566 A1 | 7/2011 | Kawchuk |
| 2011/0214279 A1 | 9/2011 | Park et al. |
| 2011/0224796 A1 | 9/2011 | Weiland et al. |
| 2011/0257653 A1 | 10/2011 | Hughes et al. |
| 2011/0257657 A1 | 10/2011 | Turner et al. |
| 2011/0295159 A1 | 12/2011 | Shachar et al. |
| 2011/0306873 A1 | 12/2011 | Shenai et al. |
| 2012/0022357 A1 | 1/2012 | Chang et al. |
| 2012/0027261 A1 | 2/2012 | Frank et al. |
| 2012/0035611 A1 | 2/2012 | Kave |
| 2012/0123301 A1 | 5/2012 | Connor et al. |
| 2012/0143090 A1 | 6/2012 | Hay et al. |
| 2012/0150243 A9 | 6/2012 | Crawford et al. |
| 2012/0172884 A1 | 7/2012 | Zheng et al. |
| 2012/0203289 A1 | 8/2012 | Beerens et al. |
| 2013/0079678 A1 | 3/2013 | Stein et al. |
| 2013/0079679 A1 | 3/2013 | Roche et al. |
| 2013/0079790 A1 | 3/2013 | Stein et al. |
| 2013/0131486 A1 | 5/2013 | Copf et al. |
| 2013/0345718 A1 | 6/2013 | Crawford et al. |
| 2013/0211531 A1* | 8/2013 | Steines .................... A61F 2/38 623/20.14 |
| 2013/0245631 A1 | 9/2013 | Bettenga |
| 2013/0253599 A1 | 9/2013 | Gorek et al. |
| 2013/0268007 A1 | 10/2013 | Rezach et al. |
| 2013/0303883 A1 | 11/2013 | Zehavi et al. |
| 2014/0100579 A1 | 4/2014 | Kelman et al. |
| 2014/0135658 A1 | 5/2014 | Hladio et al. |
| 2014/0180415 A1 | 6/2014 | Koss |
| 2014/0194889 A1 | 7/2014 | Chang et al. |
| 2014/0228670 A1 | 8/2014 | Justis et al. |
| 2014/0228860 A1* | 8/2014 | Steines ................. A61B 34/30 606/130 |
| 2014/0244220 A1 | 8/2014 | McKinnon et al. |
| 2014/0257402 A1 | 9/2014 | Barsoum |
| 2014/0272881 A1 | 9/2014 | Barsoum |
| 2014/0277149 A1 | 9/2014 | Rooney |
| 2014/0296860 A1 | 10/2014 | Stein et al. |
| 2014/0303672 A1 | 10/2014 | Tran et al. |
| 2014/0316468 A1 | 10/2014 | Keiser et al. |
| 2015/0057756 A1 | 2/2015 | Lang et al. |
| 2015/0066145 A1 | 3/2015 | Rogers et al. |
| 2015/0080901 A1 | 3/2015 | Stein |
| 2015/0081029 A1 | 3/2015 | Bojarski et al. |
| 2015/0088030 A1 | 3/2015 | Gharib et al. |
| 2015/0100066 A1 | 4/2015 | Kostrezewski et al. |
| 2015/0100091 A1 | 4/2015 | Tohmeh et al. |
| 2015/0105782 A1 | 4/2015 | D'Lima et al. |
| 2015/0127055 A1 | 5/2015 | Dvorak et al. |
| 2015/0150646 A1 | 6/2015 | Pryor et al. |
| 2015/0164657 A1 | 6/2015 | Miles et al. |
| 2015/0182292 A1 | 7/2015 | Hladio et al. |
| 2015/0223900 A1 | 8/2015 | Wiebe et al. |
| 2015/0245844 A1 | 9/2015 | Kennedy et al. |
| 2015/0250597 A1 | 9/2015 | Lang et al. |
| 2015/0265291 A1 | 9/2015 | Wilkinson |
| 2015/0305878 A1 | 10/2015 | O'Neil et al. |
| 2015/0305891 A1 | 10/2015 | Bergin et al. |
| 2015/0313723 A1 | 11/2015 | Jansen et al. |
| 2015/0328004 A1 | 11/2015 | Mahfouz |
| 2015/0366630 A1 | 12/2015 | Gorek et al. |
| 2016/0000571 A1 | 1/2016 | Mahfouz |
| 2016/0007983 A1 | 1/2016 | Frey et al. |
| 2016/0015465 A1 | 1/2016 | Steines et al. |
| 2016/0022176 A1 | 1/2016 | Le Huec et al. |
| 2016/0022370 A1 | 1/2016 | Pavlovskaia et al. |
| 2016/0030067 A1* | 2/2016 | Frey ...................... A61B 50/33 606/86 A |
| 2016/0038161 A1 | 2/2016 | Gibson |
| 2016/0038238 A1 | 2/2016 | Kostrzewski et al. |
| 2016/0038242 A1 | 2/2016 | Lo Iacono et al. |
| 2016/0038293 A1 | 2/2016 | Slamin et al. |
| 2016/0038307 A1 | 2/2016 | Bettenga |
| 2016/0045230 A1 | 2/2016 | Lowery et al. |
| 2016/0045317 A1* | 2/2016 | Lang ................... A61F 2/30942 700/98 |
| 2016/0045326 A1 | 2/2016 | Hansen et al. |
| 2016/0058320 A1 | 3/2016 | Chien et al. |
| 2016/0058523 A1 | 3/2016 | Chien et al. |
| 2016/0074052 A1 | 3/2016 | Keppler et al. |
| 2016/0074202 A1 | 3/2016 | Reed et al. |
| 2016/0081754 A1 | 3/2016 | Kostrzewski et al. |
| 2016/0095710 A1 | 4/2016 | Juszczyk et al. |
| 2016/0100907 A1 | 4/2016 | Gomes |
| 2016/0106483 A1 | 4/2016 | Mayer et al. |
| 2016/0128847 A1 | 5/2016 | Kurtaliaj et al. |
| 2016/0143744 A1 | 5/2016 | Bojarski et al. |
| 2016/0157751 A1 | 6/2016 | Mahfouz |
| 2016/0199101 A1 | 7/2016 | Sharifi-Mehr et al. |
| 2016/0228192 A1 | 8/2016 | Jansen et al. |
| 2016/0235480 A1 | 8/2016 | Scholl et al. |
| 2016/0235493 A1 | 8/2016 | LeBoeuf, II et al. |
| 2016/0242819 A1 | 8/2016 | Simpson |
| 2016/0242857 A1 | 8/2016 | Scholl |
| 2016/0242934 A1 | 8/2016 | Van der Walt et al. |
| 2016/0256279 A1 | 9/2016 | Sanders et al. |
| 2016/0256285 A1 | 9/2016 | Jansen |
| 2016/0262800 A1 | 9/2016 | Scholl et al. |
| 2016/0262895 A1 | 9/2016 | Shea et al. |
| 2016/0270802 A1 | 9/2016 | Fang et al. |
| 2016/0270931 A1 | 9/2016 | Trieu |
| 2016/0274571 A1 | 9/2016 | LaVallee et al. |
| 2016/0283676 A1 | 9/2016 | Kelly et al. |
| 2016/0287395 A1 | 10/2016 | Khalili et al. |
| 2016/0296285 A1 | 10/2016 | Chaoui et al. |
| 2016/0310221 A1 | 10/2016 | Bar et al. |
| 2016/0331417 A1 | 11/2016 | Trautwein et al. |
| 2016/0354009 A1 | 12/2016 | Schroeder |
| 2016/0354161 A1 | 12/2016 | Deitz |
| 2016/0360997 A1 | 12/2016 | Yadav et al. |
| 2017/0000568 A1 | 1/2017 | O'Neil et al. |
| 2017/0007145 A1 | 1/2017 | Gharib et al. |
| 2017/0007328 A1 | 1/2017 | Cattin et al. |
| 2017/0007408 A1 | 1/2017 | Fitz et al. |
| 2017/0027590 A1 | 2/2017 | Amiot et al. |
| 2017/0027617 A1 | 2/2017 | Strnad |
| 2017/0035580 A1 | 2/2017 | Murphy |
| 2017/0056179 A1 | 3/2017 | Lorio |
| 2017/0056196 A1 | 3/2017 | Kuiper et al. |
| 2017/0071503 A1 | 3/2017 | Wasiewlewski |
| 2017/0119472 A1 | 5/2017 | Herimann et al. |
| 2017/0132389 A1 | 5/2017 | McCaulley et al. |
| 2017/0135706 A1 | 5/2017 | Frey et al. |
| 2017/0135707 A9 | 5/2017 | Frey et al. |
| 2017/0135770 A1 | 5/2017 | Scholl |
| 2017/0143426 A1 | 5/2017 | Isaacs et al. |
| 2017/0143494 A1 | 5/2017 | Mahfouz |
| 2017/0143502 A1 | 5/2017 | Yadin et al. |
| 2017/0156798 A1 | 6/2017 | Wasielewski |
| 2017/0189121 A1 | 7/2017 | Frasier et al. |
| 2017/0231709 A1 | 8/2017 | Gupta et al. |
| 2017/0252107 A1 | 9/2017 | Turner et al. |

(56) References Cited

U.S. PATENT DOCUMENTS

| | | | |
|---|---|---|---|
| 2017/0273718 A1 | 9/2017 | Metzger et al. |
| 2017/0323037 A1 | 11/2017 | Schroeder |
| 2017/0360493 A1 | 12/2017 | Zucker et al. |
| 2018/0178148 A1 | 6/2018 | Mazor et al. |
| 2018/0235762 A1* | 8/2018 | Radermacher ...... A61F 2/30942 |
| 2018/0256067 A1 | 9/2018 | Chen et al. |
| 2018/0289396 A1 | 10/2018 | McGahan et al. |
| 2018/0295584 A1 | 10/2018 | Gliner et al. |
| 2018/0301213 A1 | 10/2018 | Zehavi et al. |
| 2018/0303552 A1 | 10/2018 | Ryan et al. |
| 2018/0310993 A1 | 11/2018 | Hobeika et al. |
| 2018/0349519 A1 | 12/2018 | Schroeder |
| 2019/0015136 A1 | 1/2019 | Kraemer |
| 2019/0046269 A1 | 2/2019 | Hedblom |
| 2019/0046287 A1 | 2/2019 | Fallin et al. |
| 2019/0059951 A1 | 2/2019 | Barrus |
| 2019/0060086 A1 | 2/2019 | Krause et al. |
| 2019/0069956 A1 | 3/2019 | Ryan et al. |
| 2019/0083144 A1 | 3/2019 | Sharifi-Mehr et al. |
| 2019/0103190 A1 | 4/2019 | Schmidt et al. |
| 2019/0110819 A1 | 4/2019 | Triplett |
| 2019/0117278 A1 | 4/2019 | Chin |
| 2019/0122364 A1 | 4/2019 | Zhang et al. |
| 2019/0142599 A1 | 5/2019 | Thibodeau |
| 2019/0167314 A1 | 6/2019 | Mosnier |
| 2019/0201013 A1 | 7/2019 | Siccardi et al. |
| 2019/0201155 A1 | 7/2019 | Gupta et al. |
| 2019/0209212 A1 | 7/2019 | Scholl |
| 2019/0223916 A1 | 7/2019 | Barrus et al. |
| 2019/0231443 A1 | 8/2019 | McGinley et al. |
| 2019/0231557 A1 | 8/2019 | Sutterlin et al. |
| 2019/0239935 A1 | 8/2019 | Willis et al. |
| 2019/0247100 A1 | 8/2019 | Mundis et al. |
| 2019/0254769 A1 | 8/2019 | Scholl |
| 2019/0262015 A1 | 8/2019 | Siccardi et al. |
| 2019/0269463 A1 | 9/2019 | Mosnier |
| 2019/0343587 A1 | 11/2019 | Mosnier |
| 2019/0362028 A1 | 11/2019 | Mosnier |

FOREIGN PATENT DOCUMENTS

| | | |
|---|---|---|
| AU | 2019200740 A1 | 2/2019 |
| AU | 2019200888 A1 | 2/2019 |
| AU | 2019203557 A1 | 6/2019 |
| CA | 2927955 | 4/2014 |
| CA | 2872845 | 1/2018 |
| CN | 1816134 | 8/2006 |
| CN | 102805677 | 12/2012 |
| CN | 104127229 | 11/2014 |
| CN | 205073000 | 3/2016 |
| CN | 103892953 | 5/2016 |
| CN | 104434287 | 1/2017 |
| CN | 104323843 | 7/2017 |
| CN | 105078555 | 11/2018 |
| EP | 1 570 781 | 7/2005 |
| EP | 2 053 580 | 4/2009 |
| EP | 2 749 235 | 7/2014 |
| EP | 2 754 419 | 7/2014 |
| EP | 2 496 183 | 9/2015 |
| EP | 3 000 443 | 3/2016 |
| EP | 2 608 749 | 8/2016 |
| EP | 2 403 434 | 4/2017 |
| EP | 3 431 032 | 1/2019 |
| FR | 1358988 | 4/1964 |
| FR | 1360208 | 5/1964 |
| JP | 2016-537036 | 12/2016 |
| JP | 2016-540610 | 12/2016 |
| SU | 1497721 | 7/1979 |
| SU | 1704102 | 1/1992 |
| WO | WO 98/55038 | 12/1998 |
| WO | WO 00/53077 | 9/2000 |
| WO | WO 04/017836 | 3/2004 |
| WO | WO 04/089224 | 10/2004 |
| WO | WO 04/111948 | 12/2004 |
| WO | WO 05/074368 | 8/2005 |
| WO | WO 06/075331 | 7/2006 |
| WO | WO 06/084193 | 8/2006 |
| WO | WO 07/035925 | 3/2007 |
| WO | WO 07/038290 | 4/2007 |
| WO | WO 09/124245 | 10/2007 |
| WO | WO 08/002588 | 1/2008 |
| WO | WO 08/079546 | 7/2008 |
| WO | WO 08/124079 | 10/2008 |
| WO | WO 09/119181 | 10/2009 |
| WO | WO 10/044880 | 4/2010 |
| WO | WO 10/064234 | 6/2010 |
| WO | WO 10/121147 | 10/2010 |
| WO | WO 10/147972 | 12/2010 |
| WO | WO 11/021192 | 2/2011 |
| WO | WO 12/012863 | 2/2012 |
| WO | WO 12/113030 | 8/2012 |
| WO | WO 12/131660 | 10/2012 |
| WO | WO 13/003435 | 1/2013 |
| WO | WO 04/030559 | 4/2014 |
| WO | WO 14/191790 | 12/2014 |
| WO | WO 16/102026 | 12/2014 |
| WO | WO 15/040552 | 3/2015 |
| WO | WO 15/054543 | 4/2015 |
| WO | WO 15/056131 | 4/2015 |
| WO | WO 15/079011 | 6/2015 |
| WO | WO 15/089118 | 6/2015 |
| WO | WO 15/185219 | 12/2015 |
| WO | WO 15/195843 | 12/2015 |
| WO | WO 15/200720 | 12/2015 |
| WO | WO 16/019424 | 2/2016 |
| WO | WO 16/019425 | 2/2016 |
| WO | WO 16/019426 | 2/2016 |
| WO | WO 16/26053 | 2/2016 |
| WO | WO 16/032875 | 3/2016 |
| WO | WO 16/044352 | 3/2016 |
| WO | WO 16/048800 | 3/2016 |
| WO | WO 16/012726 | 4/2016 |
| WO | WO 16/088130 | 6/2016 |
| WO | WO 16/094826 | 6/2016 |
| WO | WO 17/001851 | 6/2016 |
| WO | WO 16/137347 | 9/2016 |
| WO | WO 16/148675 | 9/2016 |
| WO | WO 16/165030 | 10/2016 |
| WO | WO 17/039596 | 3/2017 |
| WO | WO 17/064719 | 4/2017 |
| WO | WO 17/066518 | 4/2017 |
| WO | WO 17/077356 | 5/2017 |
| WO | WO 17/079655 | 5/2017 |
| WO | WO 17/127838 | 7/2017 |
| WO | WO 17/151949 | 9/2017 |
| WO | WO 17/221257 | 12/2017 |
| WO | WO 18/045086 | 3/2018 |
| WO | WO 18/055494 | 3/2018 |
| WO | WO 18/055518 | 3/2018 |
| WO | WO 18/078636 | 5/2018 |
| WO | WO 18/087758 | 5/2018 |
| WO | WO 18/131044 | 7/2018 |
| WO | WO 18/131045 | 7/2018 |
| WO | WO 18/183314 | 10/2018 |
| WO | WO 18/185755 | 10/2018 |
| WO | WO 18/193316 | 10/2018 |
| WO | WO 18/193317 | 10/2018 |
| WO | WO 18/203100 | 11/2018 |
| WO | WO 18/203101 | 11/2018 |
| WO | WO 19/14452 | 1/2019 |
| WO | WO 19/036039 | 2/2019 |
| WO | WO 19/043426 | 3/2019 |
| WO | WO 19/068085 | 4/2019 |
| WO | WO 19/070729 | 4/2019 |
| WO | WO 19/118844 | 6/2019 |
| WO | WO 19/140240 | 7/2019 |

OTHER PUBLICATIONS

Abe et al. "Scoliosis corrective force estimation from the implanted rod deformation using 3 D FEM analysis", 2015, Scoliosis 10(Suppl 2):52, 6 pages.

(56) References Cited

OTHER PUBLICATIONS

Aubin et al. "Preoperative Planning Simulator for Spinal Deformity Surgeries", Spine 2008, 33(20):2143-2152.

Barton et al., Mar./Apr. 2016, Early experience and initial outcomes with patient-specific spine rods for adult spinal deformity, Trending in Orthopedics, 39(2):79-86.

Fiere et al., Jul. 2016, 40. Preoperative planning and patient-specific rods for surgical treatment of thoracolumbar sagittal imbalance, in Surgery of the Spine and Spinal Cord. A Neurosurgical Approach, Van de Kalft ed., Springer International Publishing, Switzerland, pp. 645-662.

Foroozandeh et al., Summer 2012, 3D reconstruction using cubic Bezier spline curves and active contours (case study), Iranian Journal of Medical Physics, 9(3):169-176.

Galbusera et al., Feb. 2019, Artificial intelligence and machine learning in spine research, JOR Spine, 2:E1044, 20 pp.

Grove, 2011, Heterogeneous modeling of medical image data using B-spline functions, doctoral dissertation, Department of Computer Science and Engineering, University of South Florida, 212 pp.

Lazarus, Jun. 21, 2013, An introduction to splines, 29 pp.

Li et al., 2009, Modeling and measurement of 3D deformation of scoliotic spine using 2D x-ray images, Lecture Notes in Computer Science, 8 pp.

Lin, Sep. 17-21, 2003, The simplified spine modeling by 3-D Bezier curve based on the orthoaonal spinal radiographic images, Proceedinas of the 25th Annual International Conference of the IEEE EMBS, Cancun, Mexico, pp. 944-946.

Pasha et al., 2018, Data-driven classification of the 3D spinal curve in adolescent idiopathic scoliosis with an applications in surgical outcome prediction, Scientific Reports, 8:16296, 10 pp.

Poredos et al., 2015, Determination of the human spine curve based on laser triangulation, BMC Medical Imaging 15(2):1-11.

Prautzsch et al., Mar. 26, 2001, Bezier-and B-spline techniques, 58 pp.

Ratnakar et al. 2011, Predicting thoracic spinal postures in finite element model with Bezier technique, Ircobe Conference 2011, IRC-11-57, 4 pp.

Reinshagen et al. "A novel minimally invasive technique for lumbar decompression, realignment, and navigated interbody fusion", J Clin Neurosci. 2015, 22(9):1484-1490; XP055503028.

Rickert et al., "Posterior lumbar interbody fusion implants", Orthopaede. Springer Verlag, Berlin, DE vol. 44, No. 2 dated Jan. 28, 2015 pp. 162-169.

Solla et al., Mar. 2019, Patient-specific rods for surgical correction of sagittal imbalance in adults: Technical aspects and preliminary results, Clin Spine Surg, 32(2), 7 pp.

Spontech Medical AG Vertapian—die Software für Wirbelsäulenchirurgen, Aug. 29, 2013 Retrieved from the Internet: URL: https://www.youtube.com/watch?v=q0qhW1T1cp8 in 1 page.

\* cited by examiner

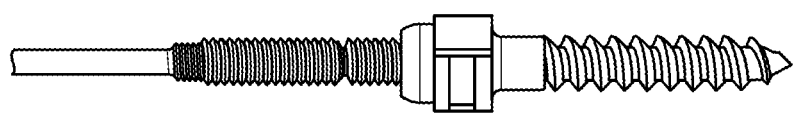
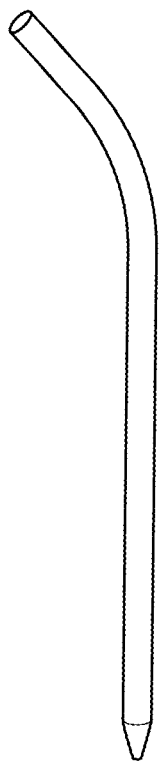
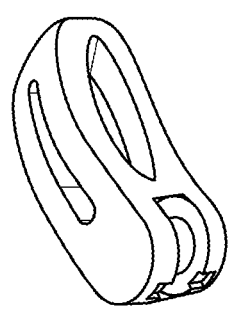
FIG. 25C
FIG. 25B
FIG. 25A

SYSTEMS, METHODS, AND DEVICES FOR DEVELOPING PATIENT-SPECIFIC MEDICAL TREATMENTS, OPERATIONS, AND PROCEDURES

CROSS-REFERENCE TO RELATED APPLICATIONS

The present application is a continuation-in-part of PCT Patent Application No. PCT/IB2017/001661, filed Dec. 12, 2017, which claims priority to U.S. Provisional Patent Application No. 62/433,102, filed Dec. 12, 2016, and U.S. Provisional Patent Application No. 62/506,855, filed May 16, 2017. The present application also claims priority to U.S. Provisional Patent Application No. 62/777,906, filed Dec. 11, 2018. Each of the foregoing applications is incorporated herein by reference in its entirety under 37 C.F.R. § 1.57.

BACKGROUND

Field

The present application relates to systems, methods, and devices for developing patient-specific medical devices, treatments, operations, and/or procedures.

Description

Spinal surgery and/or treatment are some of the most frequently performed medical procedures. Generally speaking, spinal surgery and/or treatment may involve planning prior to the treatment or surgery being performed. For example, planning may involve utilizing one or more medical images obtained of a spine of a patient to determine a particular medical device, treatment and/or surgical plan. As such, effective tools for use during the planning stage can be important in manufacturing patient personalized medical devices, developing and performing successful spinal surgery and/or treatment for a patient.

SUMMARY

Various embodiments described herein relate to systems, methods, and devices for developing patient-specific medical treatments, operations, and procedures. In some embodiments, a computer-implemented method for producing a patient-specific spinal implant comprises receiving, by a computer system, one or more pre-operative medical images of a spine of a patient; identifying, through the computer system, a posterior longitudinal ligament of the spine on the one or more pre-operative medical images; determining, by the computer system, a length of the posterior longitudinal ligament and a ligament elasticity of the posterior longitudinal ligament based on the identified posterior longitudinal ligament; determining, by the computer system, a maximum level of correction of the spine based at least in part on the determined length of the posterior longitudinal ligament and the ligament elasticity of the posterior longitudinal ligament; automatically detecting, by the computer system, one or more vertebrae on the one or more pre-operative medical images of the spine; receiving, by the computer system, one or more modifications to a vertebra of the spine on the one or more pre-operative medical images, wherein the one or more modifications comprise at least one or more of displacement or rotation of the vertebra; dynamically determining, by the computer system, whether the one or more modifications to the vertebra is within the determined maximum level of correction of the spine; dynamically updating, by the computer system, the one or more pre-operative medical images upon determination that the one or more modifications to the vertebra is within the determined maximum level of correction of the spine; generating, by the computer system, one or more desired post-operative medical images of the spine based at least in part on the dynamically updated one or more pre-operative medical images; determining, by the computer system, one or more characteristics of one or more patient-specific spinal implants for the patient based at least in part on the generated one or more desired post-operative medical images of the spine; and transmitting, by the computer system, the one or more characteristics of the one or more patient-specific spinal implants to a spinal implant production system for producing the one or more patient-specific spinal implants, wherein the computer system comprises a computer processor and an electronic storage medium.

In certain embodiments, the posterior longitudinal ligament is automatically identified by the computer system. In certain embodiments, the posterior longitudinal ligament is identified by a user tracing the posterior longitudinal ligament on the one or more pre-operative medical images of the spine.

In certain embodiments, the computer-implemented method for producing a patient-specific spinal implant comprises generating an alert, by the computer system, upon determination that the one or more modifications to the vertebra is not within the determined maximum level of correction of the spine.

In some embodiments, the one or more vertebrae is automatically detected on the one or more pre-operative medical images of the spine based at least in part on edge detection. In some embodiments, the one or more pre-operative medical images comprises an x-ray image of the spine of the patient in one or more of a flexion, extension, or neutral posture. In some embodiments, the one or more pre-operative medical images comprises one or more of an x-ray image, a CT image, or an MRI image.

In certain embodiments, the computer-implemented method for producing a patient-specific spinal implant comprises scaling the one or more pre-operative medical images. In certain embodiments, the scaling is based at least in part on a reference point or object of the one or more pre-operative medical images. In some embodiments, the one or more patient-specific spinal implants comprises one or more of a spinal rod, intervertebral spacer, cage, or screw for use in spinal surgery.

In some embodiments, a system for producing a patient-specific spinal implant comprises: one or more computer readable storage devices configured to store a plurality of computer executable instructions; and one or more hardware computer processors in communication with the one or more computer readable storage devices and configured to execute the plurality of computer executable instructions in order to cause the system to: receive one or more pre-operative medical images of a spine of a patient; identify a posterior longitudinal ligament of the spine on the one or more pre-operative medical images; determine a length of the posterior longitudinal ligament and a ligament elasticity of the posterior longitudinal ligament based on the identified posterior longitudinal ligament; determine a maximum level of correction of the spine based at least in part on the determined length of the posterior longitudinal ligament and the ligament elasticity of the posterior longitudinal ligament; automatically detect one or more vertebrae on the one or more pre-operative medical images of the spine; receive one or more modifications to a vertebra of the spine on the one or more pre-operative medical images, wherein the one or more modifications comprise at least one or more of displacement or rotation of the vertebra; dynamically determine whether the one or more modifications to the vertebra is within the determined maximum level of correction of the spine; dynamically update the one or more pre-operative medical images upon determination that the one or more modifications to the vertebra is within the determined maximum level of correction of the spine; generate one or more desired post-operative medical images of the spine based at least in part on the dynamically updated one or more pre-operative medical images; determine one or more characteristics of one or more patient-specific spinal implants for the patient based at least in part on the generated one or more desired post-operative medical images of the spine; and transmit the one or more characteristics of the one or more patient-specific spinal implants to a spinal implant production system for producing the one or more patient-specific spinal implants.

In certain embodiments, the posterior longitudinal ligament is automatically identified by the system. In certain embodiments, the posterior longitudinal ligament is identified by the system based at least in part on user input, wherein the user input comprises tracing the posterior longitudinal ligament on the one or more pre-operative medical images of the spine.

In certain embodiments, the system for producing a patient-specific spinal implant is further caused to generate an alert upon determination that the one or more modifications to the vertebra is not within the determined maximum level of correction of the spine.

In some embodiments, the one or more vertebrae is automatically detected on the one or more pre-operative medical images of the spine based at least in part on edge detection. In some embodiments, the one or more pre-operative medical images comprises an x-ray image of the spine of the patient in one or more of a flexion, extension, or neutral posture. In some embodiments, the one or more pre-operative medical images comprises one or more of an x-ray image, a CT image, or an MRI image.

In certain embodiments, the system for producing a patient-specific spinal implant is further caused to scale the one or more pre-operative medical images. In certain embodiments, the scaling is based at least in part on a reference point or object of the one or more pre-operative medical images. In some embodiments, the one or more patient-specific spinal implants comprises one or more of a spinal rod, intervertebral spacer, cage, or screw for use in spinal surgery.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

The methods summarized above and set forth in further detail below may describe certain actions taken by a practitioner; however, it should be understood that these steps can also include the instruction of those actions by another party.

BRIEF DESCRIPTION OF THE DRAWINGS

A better understanding of the devices and methods described herein will be appreciated upon reference to the following description in conjunction with the accompanying drawings, wherein:

FIG. 25A-C illustrate example implants that can be designed and/or selected for a particular patient using one or more embodiments of the systems, methods, and devices for developing patient-specific medical treatments, operations, and procedures described herein;

DETAILED DESCRIPTION

Figure 1:
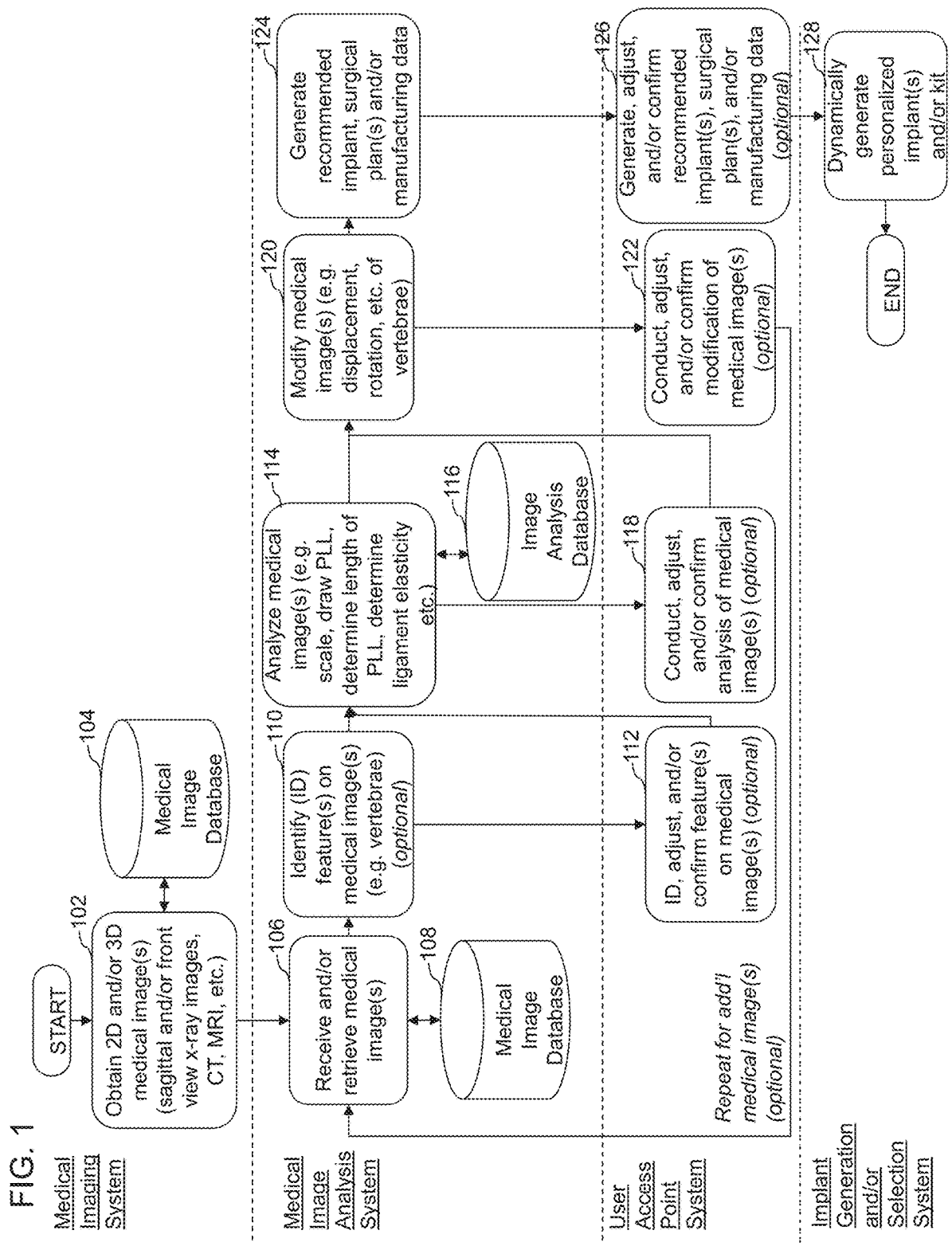
FIG. 1 is a block diagram illustrating one or more embodiments of methods for developing patient-specific medical treatments, operations, and procedures.

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

The present application relates to systems, methods, and devices for developing patient-specific medical devices, treatments, operations, and/or procedures. In particular, in some embodiments, the methods, systems, and devices described herein relate to facilitating the design and/or production of patient-specific surgical implant devices and/or selection of particular surgical implants and components for a particular patient.

Generally speaking, medical procedures, such as surgery and/or other treatments, can benefit from having accurate and/or complete patient data available to the medical practitioner prior to performing the procedure. In the context of performing operations involving manipulation of soft tissues such as ligaments within a human body, for example, it can be useful to have an understanding of the physical limitations associated with the ligaments. In a human spine, for example, factors such as ligament elasticity and/or ligament length can impact how much movement and/or adjustment can be safely performed in association with treating different vertebrae of the spine.

As an illustrative example, spinal reconstructive surgery may be used to correct anterior/posterior sagittal plane (Z-axis) imbalances ranging from abnormal (e.g., 40 mm) to severe (e.g., 90 mm) and/or to correct lateral coronal plane (X-axis) imbalances (e.g., greater than 20 mm). During such reconstructive surgery, vertical spacing between adjacent vertebrae along the length of the spine (Y-axis) may be adjusted using intervertebral spacers, rods, plates and the like.

In order to restore three-dimensional spine alignment, it can be advantageous for a medical professional to have access to and/or be able to account for quantitative measures in addition to angles, for example parameters such as LL, PI, SS, or linear measurements in other planes, such as SVA in the sagittal plane and CSVL in the coronal plane. In particular, it can be advantageous to be able to account for the Y-axis and vertical stability along the Y-axis of the human. Additional quantitative measures can be helpful to ensure neurological preservation and recovery by preventing nerve root stretch during distraction and nerve root impingement/buckling of dura during osteotomy, optimize lordotic/kyphotic expandable cage fit, and optimize neuro-foraminal volume. Other factors that may be helpful can include the tension of the posterior longitudinal ligament (PLL) and axial height.

One shortcoming of certain spinal column measurement techniques along the Y-axis can be that while overall sagittal alignment guides may be met, intervertebral spacing between a particular set of vertebrae may be severely impaired. For example, a patient may have dramatic over-distraction of two adjacent vertebrae, yet pelvic incidents, pelvic tilt, sacral slope and sagittal vertical alignment may be within a normal range. As another example, extreme shortening may occur at a specific location along the Y-axis of the spine, e.g., caused by a vertebra that is located anterior to an adjacent vertebra, yet sagittal plane SVA, coronal plane CSVL and center sacral vertical line may be within a normal range.

To address the concerns above, it can be advantageous to be able to more accurately and/or effectively model a patient area for surgery and/or other treatment and provide guidance in the treatment planning stage and/or in the man. As such, certain systems, methods, and devices are configured to dynamically model a patient area for surgery and/or other treatment, dynamically identify one or more features and/or characteristics thereon such as the length and/or elasticity of the posterior longitudinal ligament (PLL), dynamically allow modification of the model, dynamically limit and/or assist in modification of the model, and/or dynamically generate guidelines for generation of patient-specific implant devices and/or treatment/surgical kits for a specific patient. Some embodiments described herein not only generate a model based on one or more static images, but in some embodiments are further configured to dynamically account for physical limitations. In contrast, certain techniques do not effectively account for the important physical limitations of spinal ligaments, because they simplistically reconfigure separate static images into a desired post-operative state without considering the physical feasibility of the proposed combination. Without dynamically accounting for critical physical ligament limitations in the model, adverse consequences such as ligament damage, nerve damage, and/or other soft tissue damage can occur.

Certain embodiments described herein provide enhanced, dynamic systems, methods, and devices to assist with medical procedures by providing effective models of bones and/or tissues. As such, some embodiments described herein can be employed to develop and/or implement more thorough and/or accurate models which promote better chances for achieving positive outcomes from medical procedures, such as operations performed on a spinal column or other areas of the body.

In particular, without limiting the scope of the disclosure, some embodiments of the devices, systems, and methods described herein can be used to assist in spinal surgery and/or other spinal treatment or procedures. For example, in certain situations, spinal surgery and/or treatment may involve implantation of one or more implants, such as a spinal rod, one or more cages, one or more intervertebral spacers, and/or one or more screws. As such, in some embodiments described herein, the systems, methods, and devices can be configured to assist in the design, selection, and/or production of a patient-specific spinal rod(s), patient-specific cage(s), patient-specific intervertebral spacer(s), and/or patient-specific screw(s). Moreover, in certain embodiments, the systems, methods, and devices can be configured to assist in the development and/or design of one or more patient-specific kits for use in spinal surgery and/or treatment, such as, for example, a kit comprising one or more cages, intervertebral spacers, screws, and/or spinal rods that are likely to be compatible with and/or specifically configured for that particular patient.

Further, certain types of spinal surgery and/or treatment can involve displacing, rotating, and/or otherwise modifying one or more vertebrae in the spine in order to correct for a particular deformation of the spine. Similarly, modification of one or more other bodily features can be required in treatment and/or surgery of other areas, for example, the knee, wrist, and other areas of the body. As such, it can be advantageous to be able to preoperatively plan and/or design one or more particular features and/or processes of the spinal surgery and/or treatment, such as details relating to the particular displacement, rotation, and/or other modification of one or more vertebrae during spinal surgery, without over-correcting the spine.

However, it can be difficult to accurately and/or effectively produce such a plan when simply viewing one or more static medical images. The reason for this is because static medical images do not automatically take into account certain physical limitations of a patient. For example, a spine of a particular patient may only be corrected and/or modified to a certain extent, the boundaries of which can depend on ligament length and/or ligament elasticity, such as for example of the posterior longitudinal ligament of a spine. If a spine of a patient is corrected and/or modified beyond that limit, the treatment and/or surgery may result in further complications and/or injury to the patient.

To address such concerns, some embodiments described herein can dynamically in real-time or near real-time assist a medical professional and/or other user in planning and/or designing a spinal surgery or other treatment. For example, in addition to providing static images, some embodiments can be configured to determine a maximum limit of spinal modification that is possible without substantially burdening the spine of a particular patient on a patient-by-patient basis. Based on such determination, some embodiments can be configured to assist a user in planning the spinal surgery or other treatment by limiting user-inputted modification, for example displacement and/or rotation of the vertebrae, to only allow modifications within a predetermined and/or dynamically determined physical limit and/or threshold level as dynamically determined by the system. In addition or alternatively, certain embodiments can be configured to alert and/or warn a user when a user-inputted or otherwise desired modification is approaching and/or exceeds a predetermined and/or dynamically determined physical limit and/or threshold level as determined by the system. Further, certain embodiments can be configured to automatically and/or dynamically provide one or more recommended modifications, such as displacement or rotation of one or more vertebrae, and/or surgical plan to a user. Some embodiments of the system can allow a user to confirm, adjust, modify, and/or reject one or more such recommended modifications determined by the system.

In some embodiments, the system can be configured to calculate and/or dynamically determine the maximum level of correction that is physically possible for a specific patient. In some embodiments, the system can be configured to calculate the maximum level of correction by in part performing imaging on input medical images of a patient and/or other medical data, such as historical clinical information or the like. In some embodiments, the system can be configured to graphically display on a dynamically generated user interface the calculated maximum level of correction. In some embodiments, the dynamic determination of the maximum level of correction is calculated based on a length of the posterior longitudinal ligament (PLL) or a portion thereof for the vertebral segment to be corrected. More specifically, in certain embodiments, the tension of the PLL and/or axial height along the to-be-corrected posterior side and top side of the vertebral segment(s) can be used to determine a maximum level or amount of correction that can be applied to the spine of a particular patient. The PLL and length and/or tension thereof can be specific for each patient. As such, some embodiments can be configured to receive and/or retrieve one or more medical images that comprise the PLL such that the system may determine one or more patient-specific characteristics and/or features relating to the PLL. Based on such determination and/or calculation, the system can be configured to dynamically determine one or more limits for modifying the spine and/or vertebrae and/or dynamically assist a user in developing a patient-specific spinal surgical plan and/or other treatment by ensuring that the user input or plan does not exceed the maximum correctible level as determined based at least in part on one or more features relating to the PLL.

Some embodiments can further be configured to process the user input and/or user generated surgical or treatment plan to develop and/or generate instructions for producing and/or selecting one or more patient-specific implants or kits comprising a plurality of implants. Such instructions can be computer-readable. For example, in some embodiments, such instructions can be sent to a third-party provider and/or a manufacturer that can utilize such instructions to develop, produce, and/or select one or more implants that may be specifically optimized for the particular patient.

As such, certain embodiments described herein relate to dynamic computer-based tools and techniques, which can provide effective models of bones and tissues, for example, to assist with medical procedures. As described above, in one non-limiting, illustrative example, a computer-implemented analysis and modeling tool can be programmed to account for factors such as ligament elasticity, strength, and length, among other factors or physical limitations. Further, in various embodiments described herein, a human spinal column and a human pelvis are used as vehicles for illustrating specific examples of using the present invention. However, those skilled in the art will appreciate that the tools, techniques, and methods described herein can be equally applied to other bones, tissues, or organs of a human or animal body. In addition, certain aspects of the systems, devices, methods, tools, and measurements described herein can be applied equally well to fields or industries outside of the medical or healthcare fields.

Method(s) for Developing Patient-Specific Medical Treatments, Operations, and Procedures FIG. 1 is a block diagram illustrating one or more embodiments of methods for developing patient-specific medical treatments, operations, and procedures. As illustrated in FIG. 1, in some embodiments, a medical imaging analysis system can be in communication with one or more medical imaging systems, user access point systems, and/or implant generation and/or selection systems. One or more processes or techniques described in relation to FIG. 1 may be optional and/or repeated.

As illustrated in FIG. 1, in some embodiments, a medical imaging system can obtain one or more medical images of a particular patient at block 102. The medical image can be a two dimensional and/or a three dimensional medical image. The medical image obtained of the patient can be for a particular area for treatment, such as for example the spine, pelvis, and/or any other area. The medical image can be an x-ray image, a CT image, and MRI image and/or an image obtained by any other medical imaging technology available now or in the future. For example, in some embodiments, the one or more medical images can comprises one or more sagittal and/or frontal view x-ray images of the spine of a patient. In certain embodiments, the one or more medical images that are obtained by the medical imaging system at block 102 can be stored in a medical image database 104.

In certain embodiments, a medical image analysis system can be configured to receive and/or retrieve one or more medical images at block 106. For example, in some embodiments, the medical image analysis system can be configured to receive one or more medical images from a medical imaging system as described above in relation to block 102. In addition or alternatively, in certain embodiments, the medical image analysis system can be configured to retrieve one or more medical images from a medical image database 108. The medical image database 108 can be the same and/or different from the medical image database 104.

In some embodiments, based on the one or more medical images, the medical image analysis system can be configured to identify one or more features on the one or more medical images at block 110. For example, for a spinal medical image, the medical image analysis system can be configured to automatically and/or dynamically identify the presence, location and/or boundaries of one or more vertebrae, for example, by utilizing edge detection technology. Alternatively and/or in addition to automatic and/or dynamic identification of one or more features by the medical image analysis system, in some embodiments, a user may, through a user access point system, identify one or more features on the one or more medical images, such as the vertebrae of a medical image of a spine, at block 112. Further, in certain embodiments, the user can adjust and/or confirm one or more features on the one or more medical images that were identified by the medical image analysis system through a user access point system at block 112.

In certain embodiments, the medical image analysis system can be configured to analyze the one or more medical images at block 114. For example, the medical image analysis system can be configured to scale the one or more medical images in certain embodiments. Scaling of the one or more medical images can be automatically and/or dynamically performed in some embodiments. In certain embodiments, scaling of the one or more medical images can be configured to be manually and/or at least manually performed in combination with an automatic and/or dynamic scaling feature or process. In some embodiments, scaling of the one or more medical images can involve utilization of a reference point or object with a known size that can be made part of the medical image at block 102. In certain embodiments, scaling of the one or more medical images can involve identification of a particular reference point and/or feature on the body of the patient.

In addition, in certain embodiments, the medical image analysis system can be configured to analyze the one or more medical images at block 114 by identifying and/or tracing or drawing the posterior longitudinal ligament (PLL) or a portion thereof on a vertebral segment to be corrected. In certain embodiments, the medical image analysis system can further be configured to dynamically and/or automatically determine the length, strength, elasticity, diameter, and/or any other feature or characteristic of the PLL or a portion thereof. In certain embodiments, the results of one or more analyses conducted by the medical image analysis system of the one or more medical images can be stored and an image analysis database 116, for example for future reference. In some embodiments, analysis of the one or more medical images, such as identification and/or analysis of one or more features of the PLL can be based at least in part on certain pre-inputted analysis criteria, which can comprise analysis provided from literature.

In some embodiments, the system can allow a user to conduct, adjust, and/or confirm one or more analyses of the one or more medical images conducted by the medical image analysis system through a user access point system at block 118. For example, in some embodiments, the system can be configured to allow a user through a user access point system to conduct, adjust, confirm, and/or reject the scaling of one or more medical images. In addition, in some embodiments, the system can be configured to allow a user through a user access point system to draw and/or trace a PLL (or a portion thereof) on a spinal image of a patient, and/or confirm, adjust, modify, and/or reject a PLL or a portion thereof on a spinal image automatically and/or dynamically traced or identified by the medical image analysis system. Further, in certain embodiments, the system can be configured to allow a user through a user access point system to determine the length, elasticity, strength, and/or other feature of the PLL. In some embodiments, the system can be configured to allow a user through a user access point system to adjust, modify, confirm, and/or reject the length, elasticity, strength, and/or other feature of the PLL as automatically and/or dynamically determined by the medical image analysis system.

In some embodiments, the medical image analysis system can be configured to modify the one or more medical images at block 120. For example, for an image of a spine of a patient, the medical image analysis system can be configured to dynamically and/or automatically displace, rotate, and/or otherwise modify one or more vertebrae to correct for a particular spinal condition of a patient based on one or more analysis of the medical images. For example, based at least in part on the one or more analyses that was conducted of the one or more medical images, the medical image analysis system can be configured to determine that one or more vertebrae of the spine of the patient should be corrected in a certain manner when performing a spinal correction surgery and/or treatment of that patient. The system can be configured to dynamically and/or automatically modify the medical image(s) based at least in part of studies and/or results from literature and/or data collected or analyzed previously by the system.

In certain embodiments, the system can allow a user to conduct one or more modifications of the medical image at block 122 through a user access point system. For example, the system can be configured to allow a user to move and/or rotate one or more vertebrae on the medical image(s). In addition or alternatively, the system can allow a user to confirm, adjust, and/or reject one or more modifications of the one or more medical images dynamically and/or automatically conducted by the medical image analysis system. For example, in some embodiments, the system can allow a user through a user access point system to review displacement, rotation, and/or other modification of one or more vertebrae as dynamically and/or automatically determined by the medical image analysis system.

In some embodiments, depending on the number of medical images available for the particular patient, the system can be optionally configured to repeat one or more processes described in relation to one or more blocks between blocks 106 and block 122 in order to perform one or more analyses on a plurality of medical images. For example, in some embodiments, the system can be configured to repeat processes described in relation to one or more blocks between blocks 106 and block 122 for a sagittal and/or frontal view x-ray image. In other embodiments, the system can be configured to repeat processes described in relation to one or more blocks between blocks 106 and block 122 for an x-ray image, CT image, and/or MRI image of the same patient. Furthermore, in some embodiments, the system can be configured to repeat processes described in relation to one or more blocks between blocks 106 and block 122 for one or more x-ray images or other medical images of the same area of a patient depending on the posture of the patient. For example, in some embodiments, the system can be configured to repeat processes described in relation to one or more blocks between blocks 106 and block 122 for an x-ray image of a spine of a patient when in a flexion posture, neutral posture, and/or extended posture. By doing so, a more robust and/or more complete analysis of the patient can be obtained.

In some embodiments, based on at least one or more of the identified features, analyses of the medical image, and/or modification thereof, the medical image analysis system can be configured to further automatically and/or dynamically generate one or more recommended implants, components thereof, kits thereof, and/or surgical plans for the patient at block 124. In certain embodiments, the system can be configured to automatically and/or dynamically generate manufacturing instructions data for manufacturing and/or selecting the one or more recommended implants and/or kits at block 124. For example, in some embodiments, the system can be configured to specify features of a patient-specific spinal rod for implantation, which may comprise the diameter, length, and/or curvature of the spinal rod. Similarly, in certain embodiments, the system can be configured to specify features of a patient-specific cages or intervertebral spacers for implantation, which may comprise the height, length, thickness, and/or other dimension(s) of the cage or intervertebral spacer. Further, in some embodiments, the system can be able to recommend that one or more particular screws, rods, intervertebral spacers, and/or cages be included in a surgical kit and/or treatment kit for a particular patient at block 124.

In certain embodiments, the system can be configured to allow a user to generate one or more recommended implants, components thereof, kits thereof, manufacturing instructions data thereof, and/or surgical plans for the patient at block 126 through a user access point system. In some embodiments, the system can be configured to allow a user to confirm, modify, adjust, and/or reject one or more recommended implants, components thereof, kits thereof, manufacturing instructions data thereof, and/or surgical plans for the patient as dynamically and/or automatically generated by the medical image analysis system.

In some embodiments, the generated one or more surgical plans, recommended implants, components and/or kits thereof and/or manufacturing instructions data thereof can be electronically transmitted to an implant generation and/or selection system. The implant generation and/or selection system can be configured to automatically and/or dynamically generate one or more personalized implants and/or kits for the particular patient at block 128, which can comprise one or more spinal rods, screws, cages, intervertebral spacers, or the like.

Figure 2:
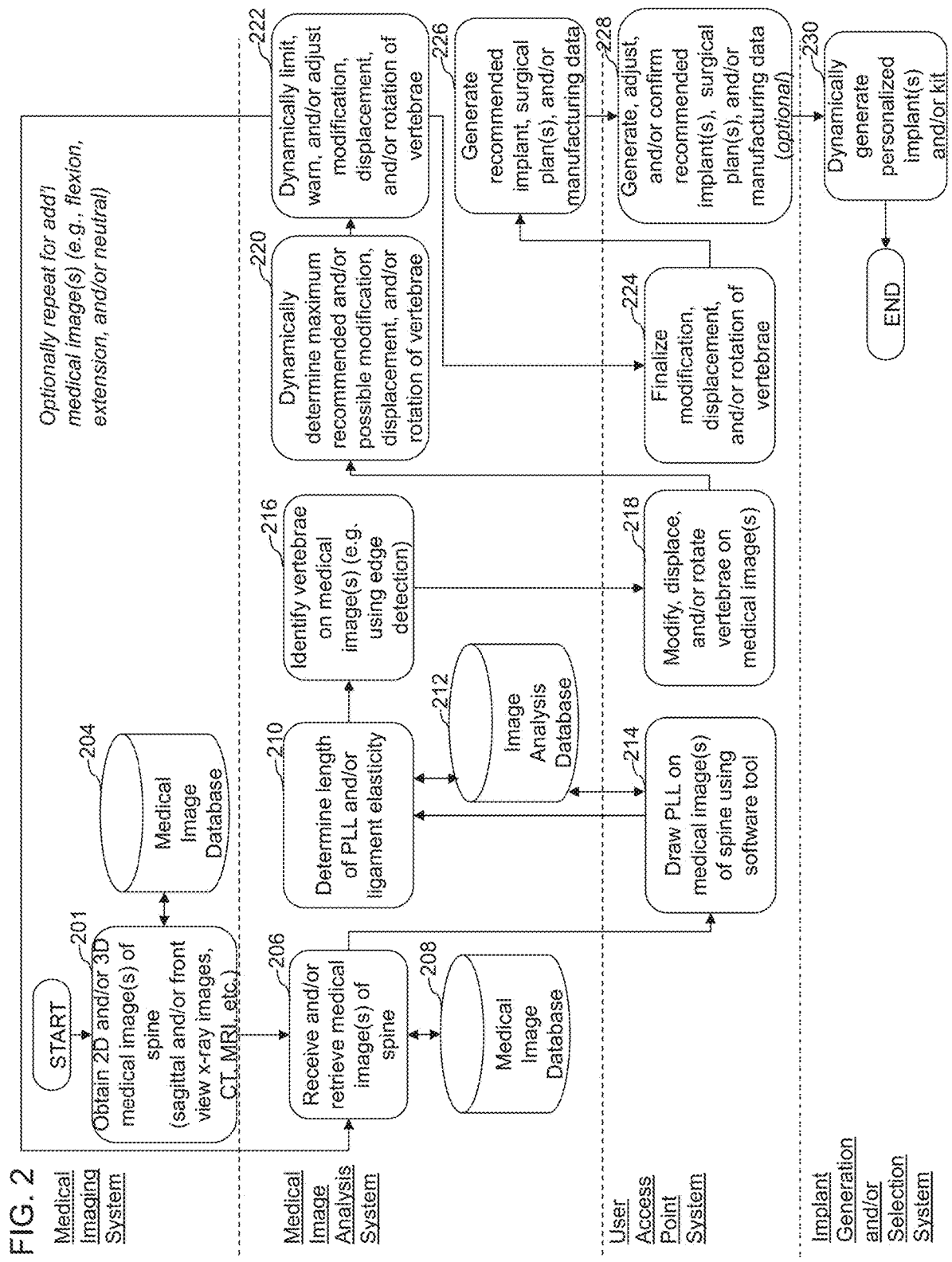
FIG. 2 is a block diagram illustrating one or more embodiments of methods for developing patient-specific medical treatments, operations, and procedures.

FIG. 2 is a block diagram illustrating one or more embodiments of methods for developing patient-specific medical treatments, operations, and procedures. In some embodiments, a medical imaging system can be configured to obtain one or more two dimensional and/or three dimensional medical images of the spine of a patient at block 201, in a similar manner as described above in relation to FIG. 1. In certain embodiments, the one or more two dimensional and/or three dimensional medical images of the spine, such as for example sagittal and/or frontal view x-ray image(s), CT image(s), and/or MRI image(s) can be configured to be stored in a medical image database 204.

In certain embodiments, a medical image analysis system can be configured to receive the obtained one or more medical images at block 206. Alternatively and/or in addition to the above, in some embodiments, the medical image analysis system can be configured to retrieve one or more medical images of the spine at block 206, for example, from a medical image database 208. The medical image database 208 can be the same and/or different from the medical image database 204.

In some embodiments, a user access point system in electronic communication with the medical image analysis system can be configured to display the one or more medical images of the spine for viewing by a user. In certain embodiments, the user access point system can be configured to allow a user to identify, draw and/or trace a PLL or a portion thereof of the spine on the one or more medical images, for example using a software tool at block 214. In certain embodiments, the PLL traced by a user can be stored in an image analysis database 212.

Based on the traced and/or drawn PLL, the medical image analysis system in certain embodiments can be configured to automatically and/or dynamically determine one or more features of the PLL at block 210, such as for example the length, strength, and/or elasticity of the PLL or a portion thereof. The determined length, strength, and/or elasticity of the PLL or a portion thereof can be stored in the image analysis database 212.

In some embodiments, the medical image analysis system can be configured to identify one or more vertebrae on the one or more medical images, for example by using edge detection techniques at block 216. The medical image analysis system can further be configured to identify one or more other features on the one or more medical images as well, such as for example, a PLL, intervertebral spacing(s), or the like.

In some embodiments, the system can be configured to allow a user through a user access point system to modify, displace, and/or rotate one or more vertebrae on the one or more medical images at block 218. For example, in some embodiments, the system may allow a user to click and drag or otherwise move or rotate one or more vertebrae on the spinal image to view a simulated post-operative or post-treatment view.

In some embodiments, the medical image analysis system can be configured to automatically and/or dynamically determine a maximum recommended and/or possible modification, displacement, and/or rotation of one or more vertebrae and/or the overall spine of the patient at block 220. For example, in some embodiments, the medical image analysis system can be configured to use the determined length, strength, and/or elasticity of the PLL or a portion thereof to dynamically and/or automatically determine how much the spine of the particular patient can be corrected and/or modified without substantially burdening the spine.

In certain embodiments, the limits of vertebral correction and/or one or more variables thereof can be pre-configurable. For example, in some embodiments, the system can be configured such that a particular vertebral segment may only be modified up to the total length of the PLL of that vertebral segment and/or such that the total length of the PLL of that vertebral segment remains substantially constant post-modification. In certain embodiments, the system can be configured such that a particular vertebral segment may only be modified up to a certain percentage of the total length of the PLL of that vertebral segment as determined by the elasticity of the PLL. For example, in some embodiments, the system can be configured such that a particular vertebral segment may only be modified such that the post-modification length of the PLL of that vertebral segment is at or below the pre-modification length of the PLL of that vertebral segment or a percentage thereof, wherein the percentage is about 70%, about 80%, about 90%, about 91%, about 92%, about 93%, about 94%, about 95%, about 96%, about 97%, about 98%, about 99%, about 100%, about 101%, about 102%, about 103%, about 104%, about 105%, about 106%, about 107%, about 108%, about 109%, about 110%, about 120%, about 130%, and/or within a range defined by two of the aforementioned values.

In some embodiments, the medical image analysis system can be configured to dynamically limit, warn, and/or adjust modification displacement and/or rotation of the vertebrae at block 222. For example, if a user attempts to displace a vertebra beyond level determined by the system and/or preconfigured to be an allowable maximum or recommended level, the system, in some embodiments, can be configured to disallow and/or prevent movement or other modification of the vertebra past that level. In other embodiments, the system can be configured to warn the user that the user is approaching and/or exceeding the limit, for example, through generating one or more graphical warnings and/or audio. Furthermore, in some embodiments, the limit for modifying a particular vertebra can be dependent on one or more modifications of other vertebrae. For example, if a user attempts to modify a second vertebra in a certain manner after modifying a first vertebra, modification of the second vertebra might not be within the recommended or maximum allowable limit even though the modification of the second vertebra by itself may be within the recommended or maximum allowable limit when taken alone. As such, in some embodiments, the system can be configured to dynamically update its determination based on already existing modifications to determine whether a subsequent modification is acceptable and/or within a determined recommended or maximum limit.

In some embodiments, one or more processes described in relation to blocks between blocks 206 and 222 can be repeated optionally for one or more additional medical images. For example, the system can be configured to repeat one or more processes between blocks 206 and 222 for one or more images such as x-ray images of the spine of the same patient when the patient is in a flexion, extension and/or neutral posture.

In some embodiments, the system can allow a user to finalize the modification, displacement, and/or rotation of one or more vertebrae at block 224 through the user access point system. In certain embodiments, the medical image analysis system can be configured to automatically and/or dynamically generate one or more recommended implants, components thereof, kits thereof, and/or surgical plans for the patient at block 226, for example based on the finalized modification of vertebrae as inputted by the user. In certain embodiments, the system can be configured to automatically and/or dynamically generate manufacturing instructions data for manufacturing and/or selecting the one or more recommended implants and/or kits at block 226. More specifically, in certain embodiments, the system can be configured to specify features of a patient-specific spinal rod for implantation, which may comprise the diameter, length, and/or curvature of the spinal rod. Similarly, in certain embodiments, the system can be configured to specify features of a patient-specific cages or intervertebral spacers for implantation, which may comprise the height, length, thickness, and/or other dimension(s) of the cage or intervertebral spacer. Further, in some embodiments, the system can be able to recommend that one or more particular screws, rods, intervertebral spacers, and/or cages be included in a surgical kit and/or treatment kit for a particular patient.

In certain embodiments, the system can be configured to allow a user to generate one or more recommended implants, components thereof, kits thereof, manufacturing instructions data thereof, and/or surgical plans for the patient at block 228 through a user access point system. In some embodiments, the system can be configured to allow a user to confirm, modify, adjust, and/or reject one or more recommended implants, components thereof, kits thereof, manufacturing instructions data thereof, and/or surgical plans for the patient as dynamically and/or automatically generated by the medical image analysis system.

In some embodiments, the generated one or more surgical plans, recommended implants, components and/or kits thereof and/or manufacturing instructions data thereof can be electronically transmitted to an implant generation and/or selection system. The implant generation and/or selection system can be configured to automatically and/or dynamically generate one or more personalized implants and/or kits for the particular patient at block 230, which can comprise one or more spinal rods, screws, intervertebral spacers, cages, or the like.

Graphical User Interface and/or Display

Figure 3:
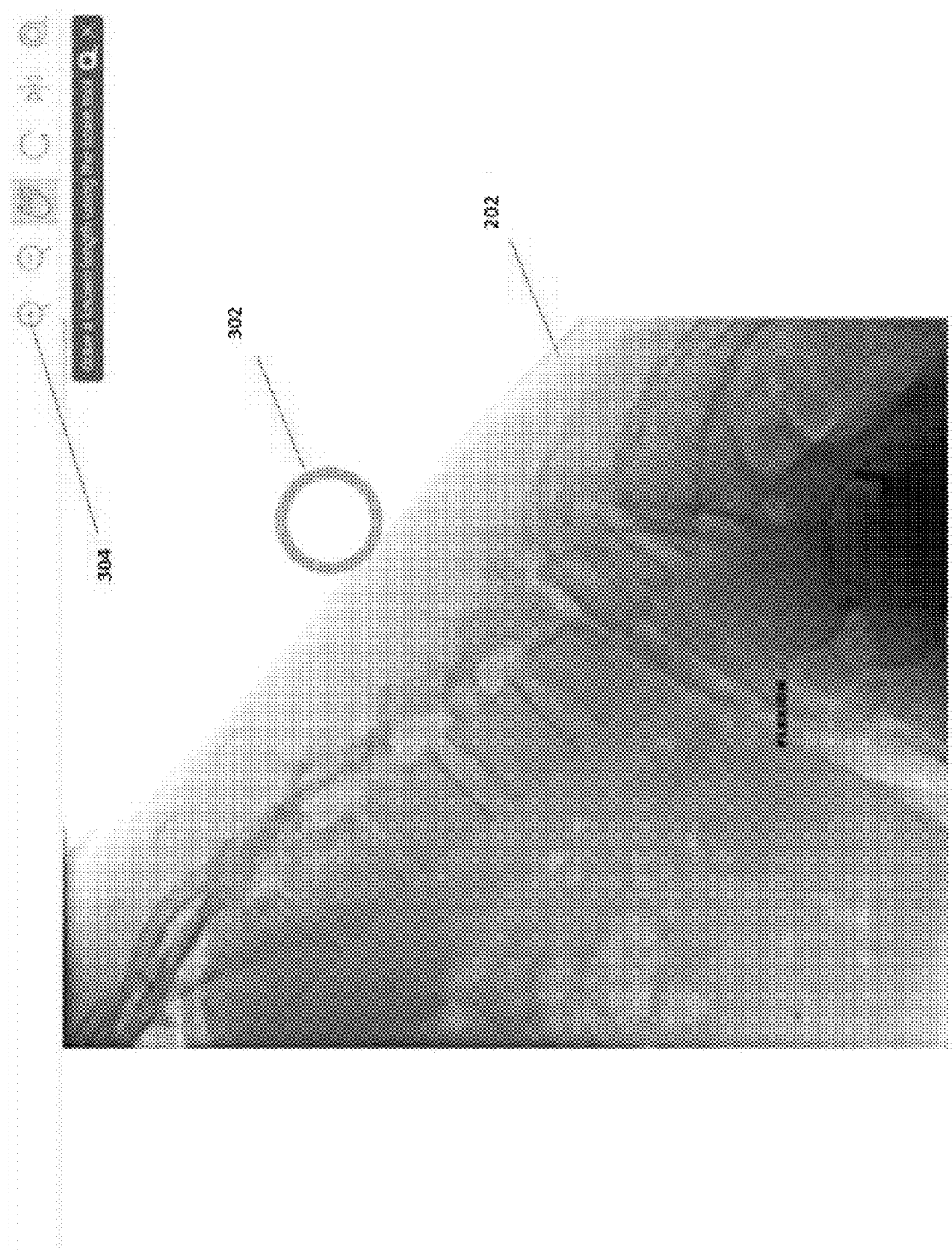
FIGS. 3 and 4 illustrate example embodiments of a graphical user interface of a system for developing patient-specific medical treatments, operations, and procedures, in which the graphical user interface comprises a reference point.
Figure 4:
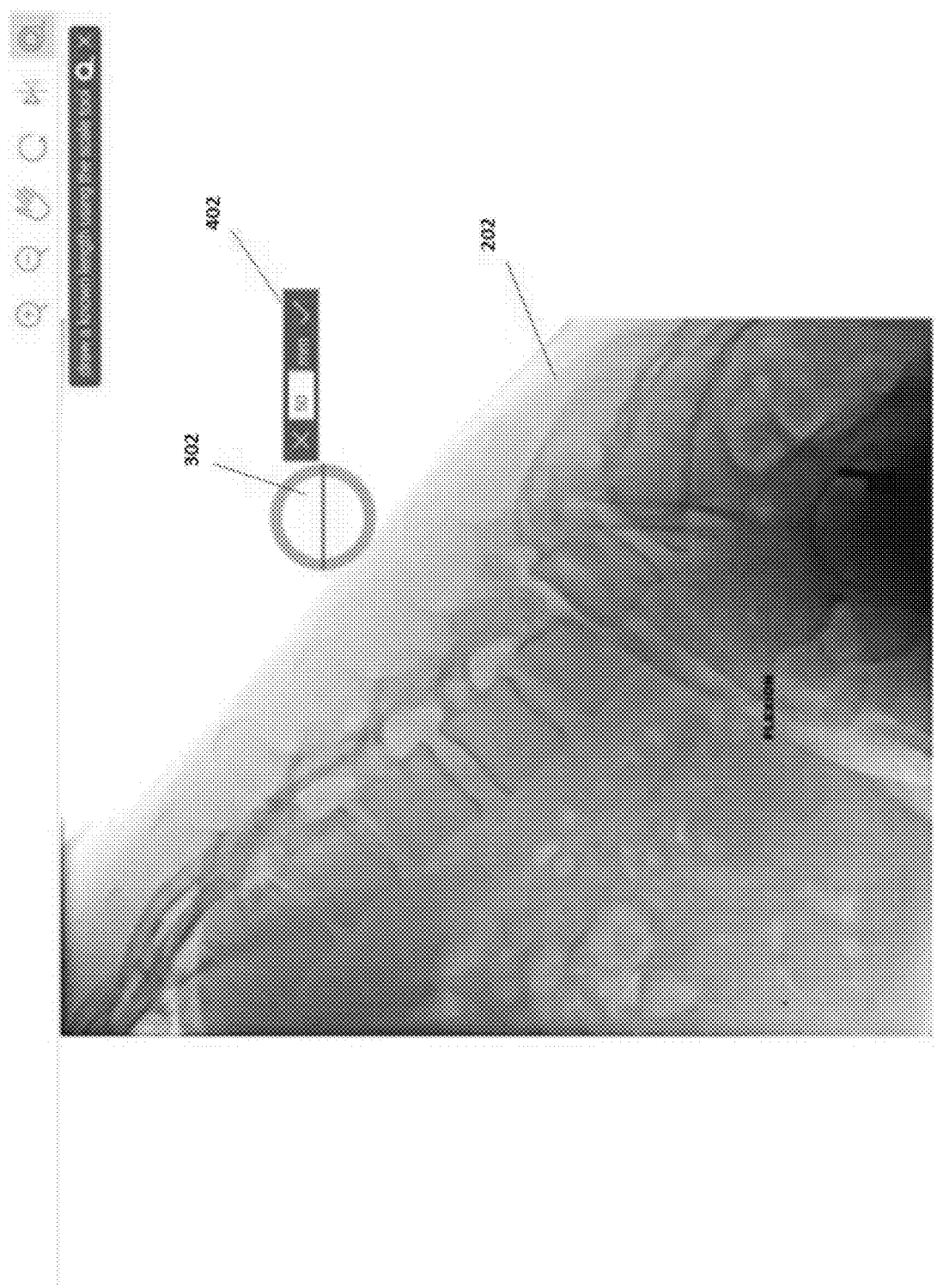

FIGS. 3 and 4 illustrate example embodiments of a graphical user interface of a system for developing patient-specific medical treatments, operations, and procedures, in which the graphical user interface comprises a reference point. In particular, as illustrated in FIGS. 3 and 4, the system can be configured to display an x-ray image of the spine of a patient or a portion thereof. The x-ray or other medical image can comprise a reference point or area 302 in some embodiments for scaling purposes. For example, in the illustrated embodiment, a steel ball 302 can be fastened to the body of the patient form which the image 202 was derived.

In the illustrated example, it can be known that the steel ball 302 measures 50 mm in diameter, which can be used as reference point for setting the drawing scale for the image 202. Using a scale tool 402, the system can allow a user to draw a line across the known 50 mm length to confirm the proper scale for further modifications or annotations to be made to the image 202. Also, as shown in FIG. 3, a toolbar 304 can be provided for performing tasks such as magnification, panning, rotation, and reflect control operations on the image 202, for example.

Figure 5:
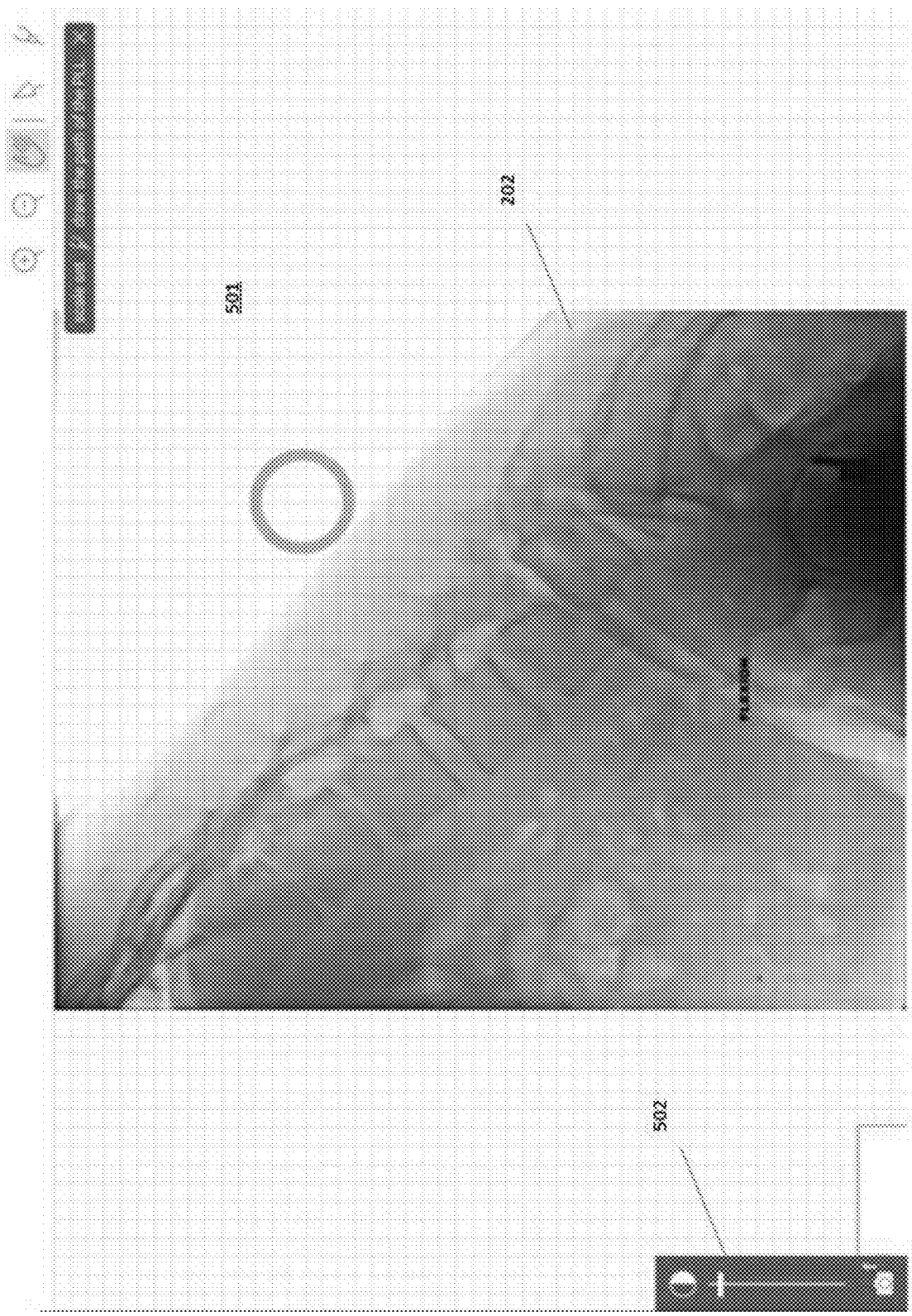
FIG. 5 illustrates an example embodiment of a graphical user interface of a system for developing patient-specific medical treatments, operations, and procedures, in which the graphical user interface comprises a grid option.

FIG. 5 illustrates an example embodiment of a graphical user interface of a system for developing patient-specific medical treatments, operations, and procedures, in which the graphical user interface comprises a grid option. As illustrated in FIG. 5, in some embodiments, the system can be configured to allow a user to add a grid 501 to a canvas of the analysis and modeling tool. The grid 501 can serve as a guide for a user drawing or positioning other annotations on the image 202. In the illustrated embodiment, a contrast control 502 can also be provided to allow the user to adjust the contrast of the image 202 as presented on a screen or display of a user access point system, such as a computer or computing device for example.

Figure 6:
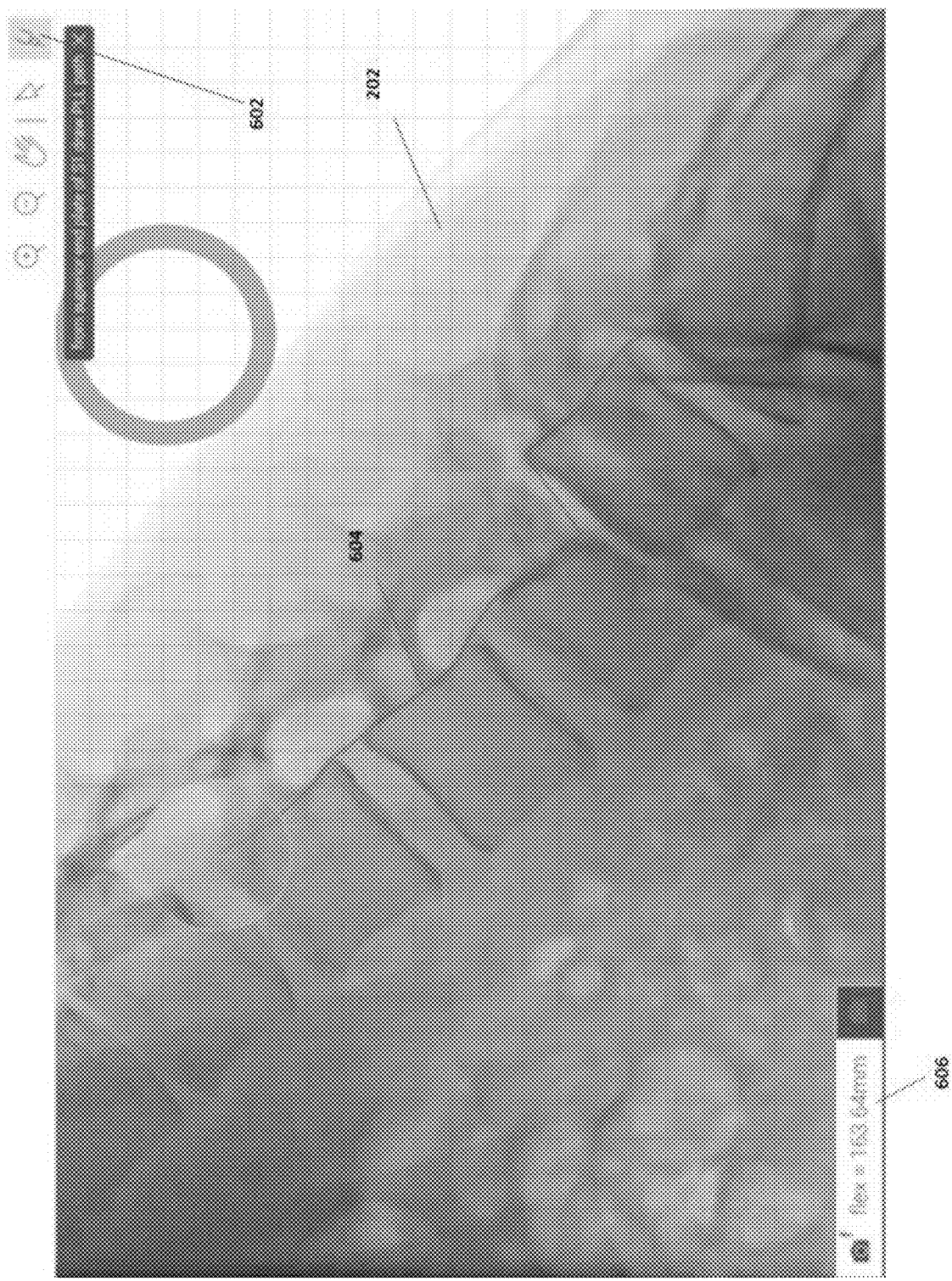
FIG. 6 illustrates an example embodiment of a graphical user interface of a system for developing patient-specific medical treatments, operations, and procedures, in which the graphical user interface comprises a graphical drawing tool.

FIG. 6 illustrates an example embodiment of a graphical user interface of a system for developing patient-specific medical treatments, operations, and procedures, in which the graphical user interface comprises a graphical drawing tool. In particular, FIG. 6 shows an example of using a drawing tool 602 of an analysis and modeling tool to draw a line 604 representing a path of a posterior longitudinal ligament ("PLL"), for example, within a portion of the spinal column shown in the image 202. As the line 604 is drawn by the user with the tool, data associated with the position of the line 604 on the image 202 can be captured and communicated to a data storage medium. The analysis and modeling tool can be programmed to calculate and display the length of the path (e.g., 163.64 mm) in the data field 606 as shown. Also, a new drawing layer can be created after the line representing the path of the PLL has been drawn.

Figure 7:
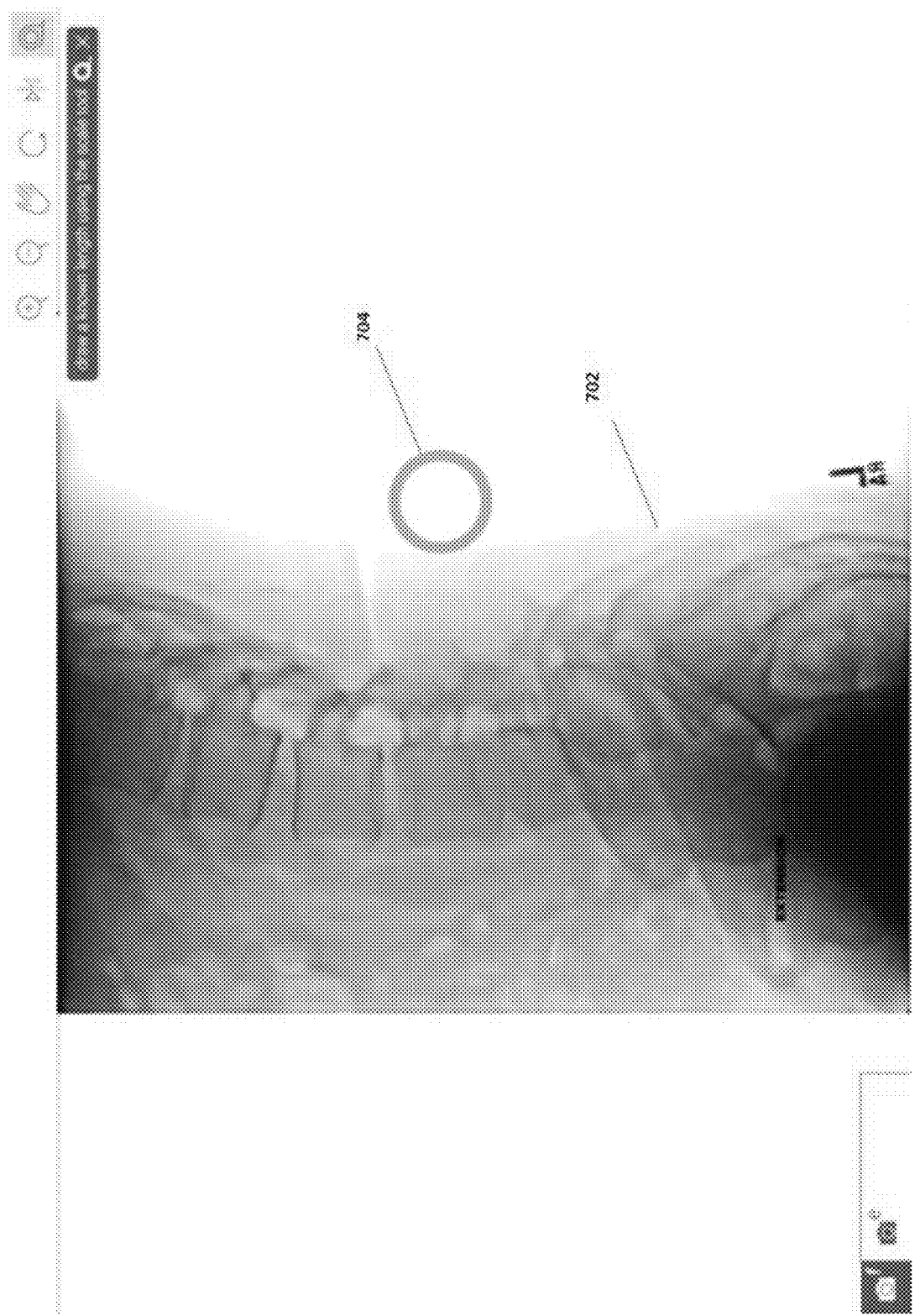
FIGS. 7-8 illustrate example embodiments of a graphical user interface of a system for developing patient-specific medical treatments, operations, and procedures, in which the system is configured to allow analysis of one or more additional images.
Figure 8:
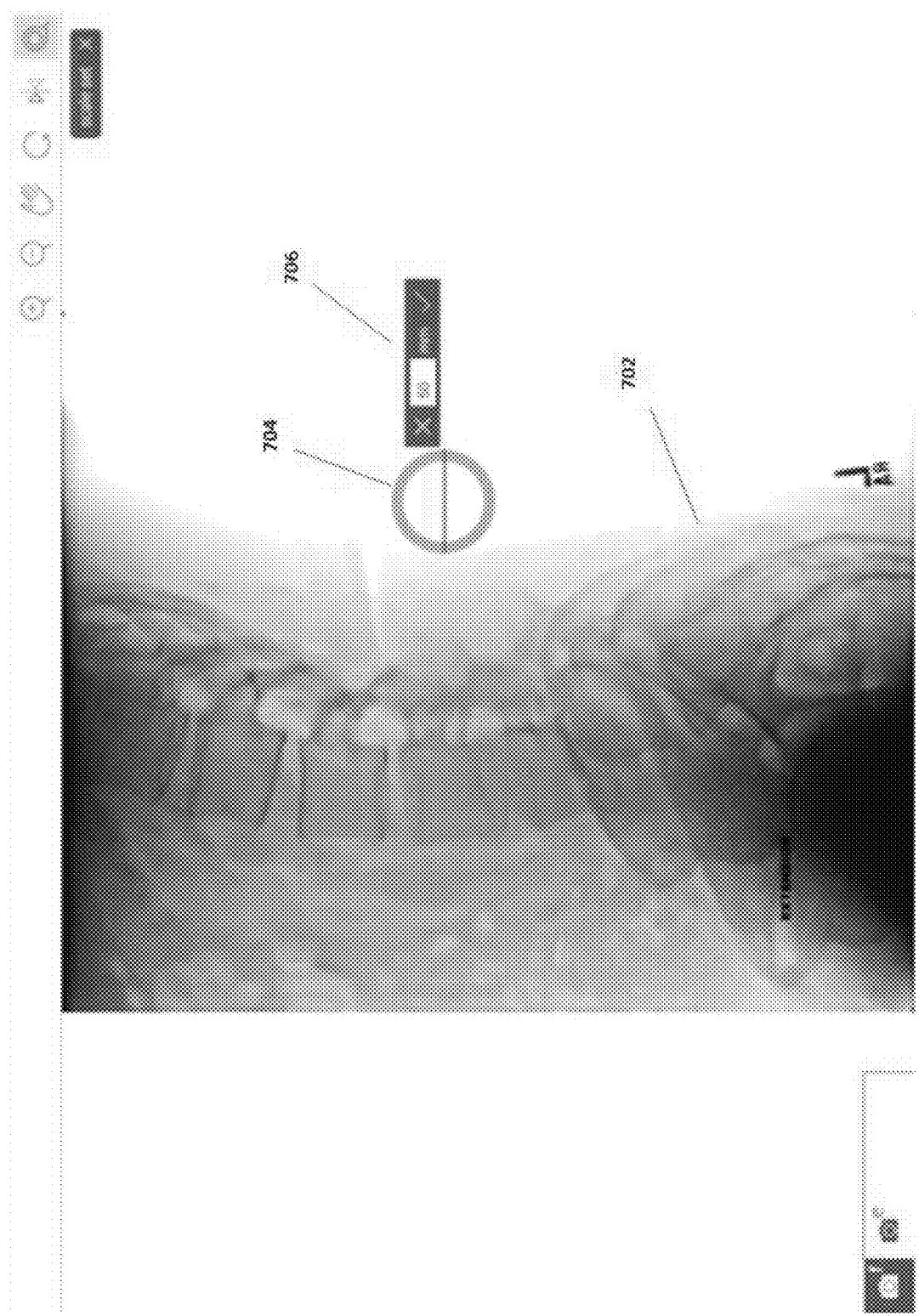

FIGS. 7-8 illustrate example embodiments of a graphical user interface of a system for developing patient-specific medical treatments, operations, and procedures, in which the system is configured to allow analysis of one or more additional images. In particular, FIGS. 7 and 8 illustrate example embodiments that allow accessing of a new drawing layer and importing a different image 702 onto the canvas of the analysis and modeling tool.

In the illustrated embodiment, the image 702 represents the spinal column of the patient in an extension state. The image 702 can be displayed with a representation of a steel ball 704 which was fastened to the body of the patient from which the image 702 was derived. In this example, the steel ball 704 measures 50 mm in diameter and can be used as reference point for setting the drawing scale for the image 702. Using the scale tool 706, the user can draw a line across the known 50 mm length (see FIG. 8) to confirm the proper scale for further modifications or annotations to be made to the image 702. It can be appreciated that, due to variance between and among scales of different images, the process of setting the drawing scale may need to be repeated for flexion, extension, and/or neutral or standing positions of the same patient. In the illustrated embodiment, links to multiple drawing layers may be provided with "f" for the flexion drawing layer, "e" for the extension drawing layer, and "n" for the neutral or standing drawing layer.

Figure 9:
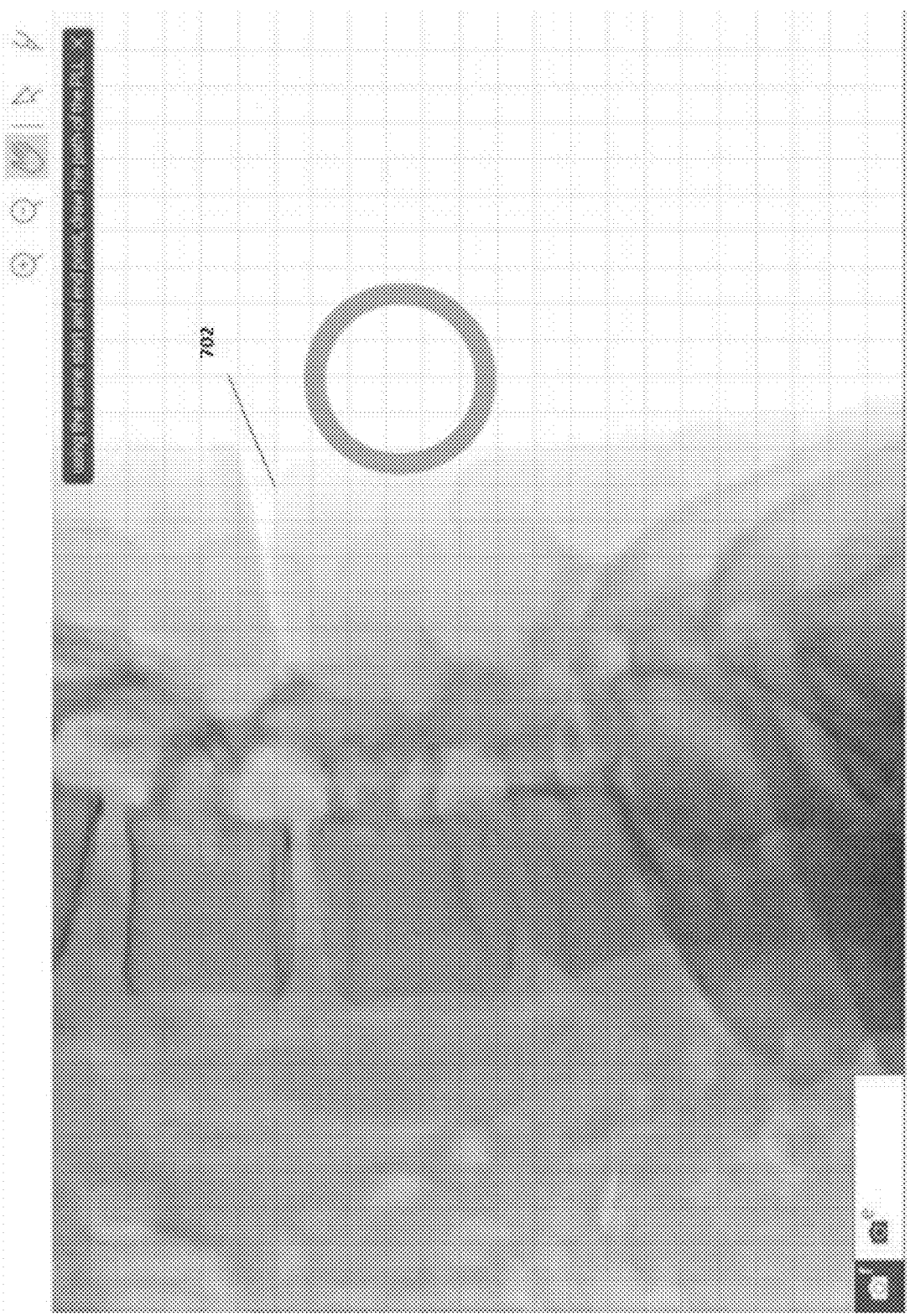
FIGS. 9-10 illustrate example embodiments of a graphical user interface of a system for developing patient-specific medical treatments, operations, and procedures, in which the graphical user interface comprises a graphical drawing tool.
Figure 10:
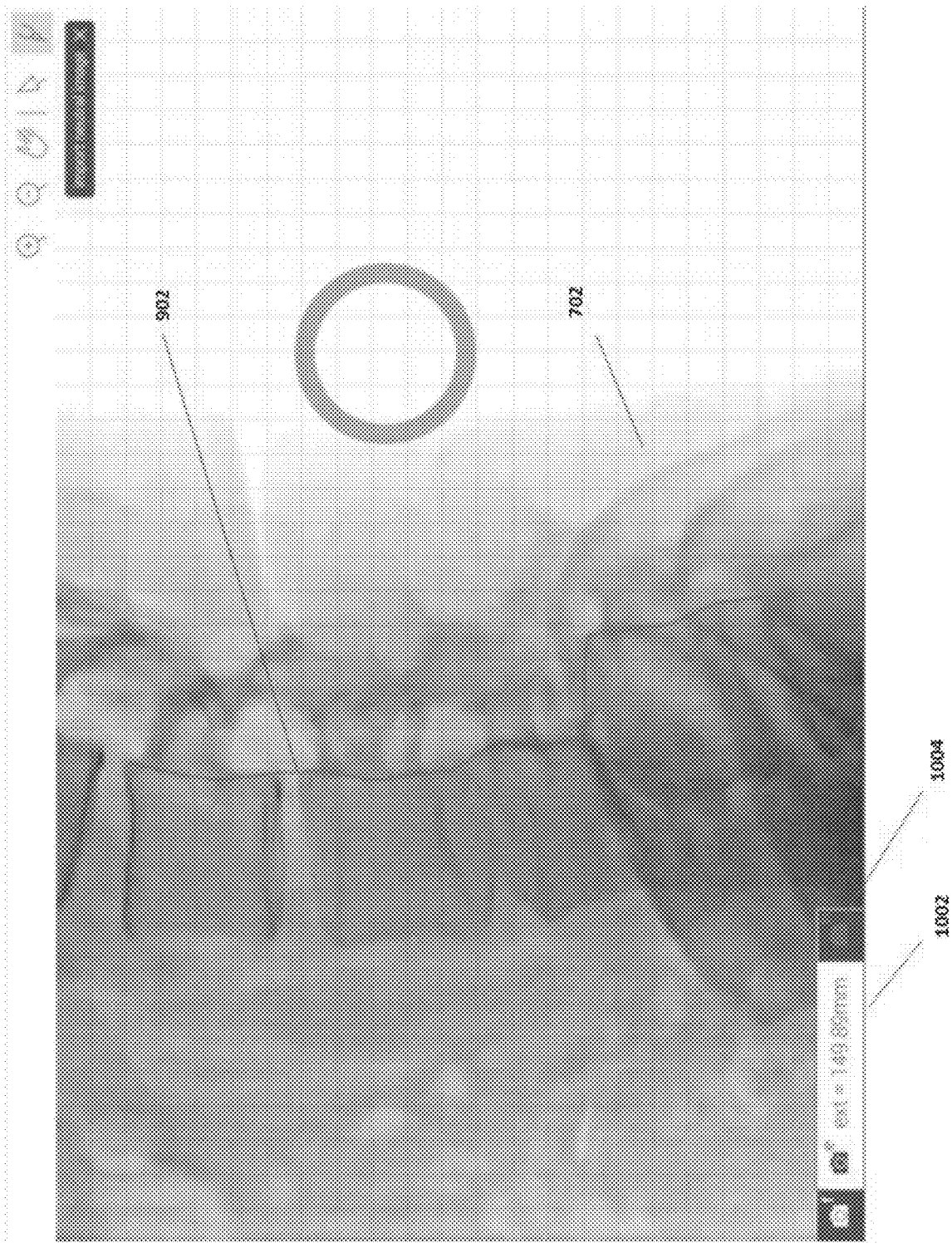

FIGS. 9-10 illustrate example embodiments of a graphical user interface of a system for developing patient-specific medical treatments, operations, and procedures, in which the graphical user interface comprises a graphical drawing tool. More specifically, FIGS. 9 and 10 illustrate example embodiments of a system configured to allow drawing a line 902 along the PLL for the image 702 using the same or similar start and end points as used for the flexion image 202.

In some embodiments, the user may be prompted to use the same or similar start and end points to promote greater accuracy for the measurement. As shown in FIG. 10, the length of the line 902 associated with the PLL in its extended position can be displayed in a data field 1002. In certain embodiments, completion of the line 902 for the image 702 can result in the analysis and modeling tool generating a link 1004 for a new drawing layer. In some embodiments, the new drawing layer may be configured to prompt the user to import a neutral or standing image onto the canvas of the analysis and modeling tool.

Figure 11:
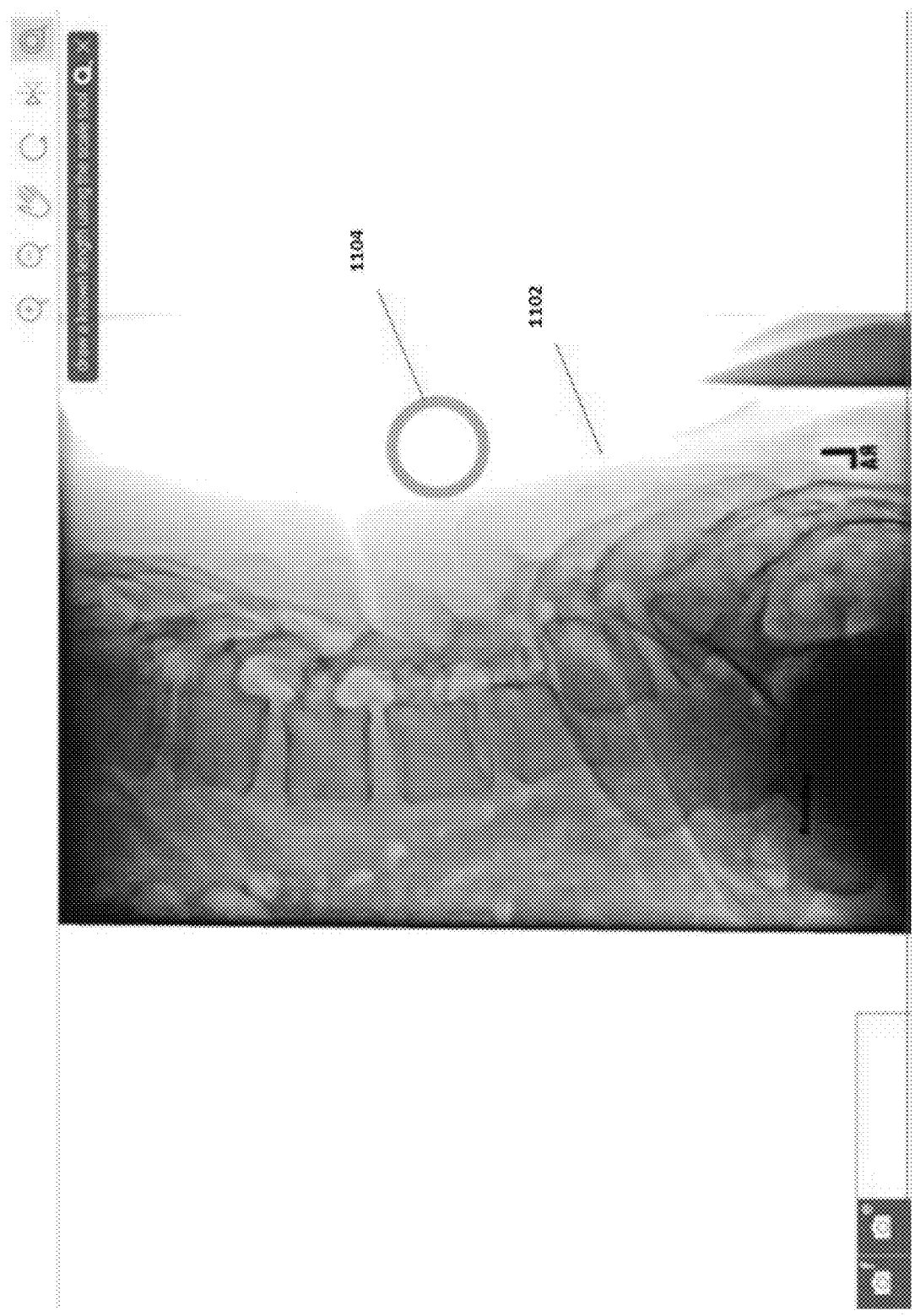
FIGS. 11-12 illustrate example embodiments of a graphical user interface of a system for developing patient-specific medical treatments, operations, and procedures, in which the system is configured to allow analysis of one or more additional images.
Figure 12:
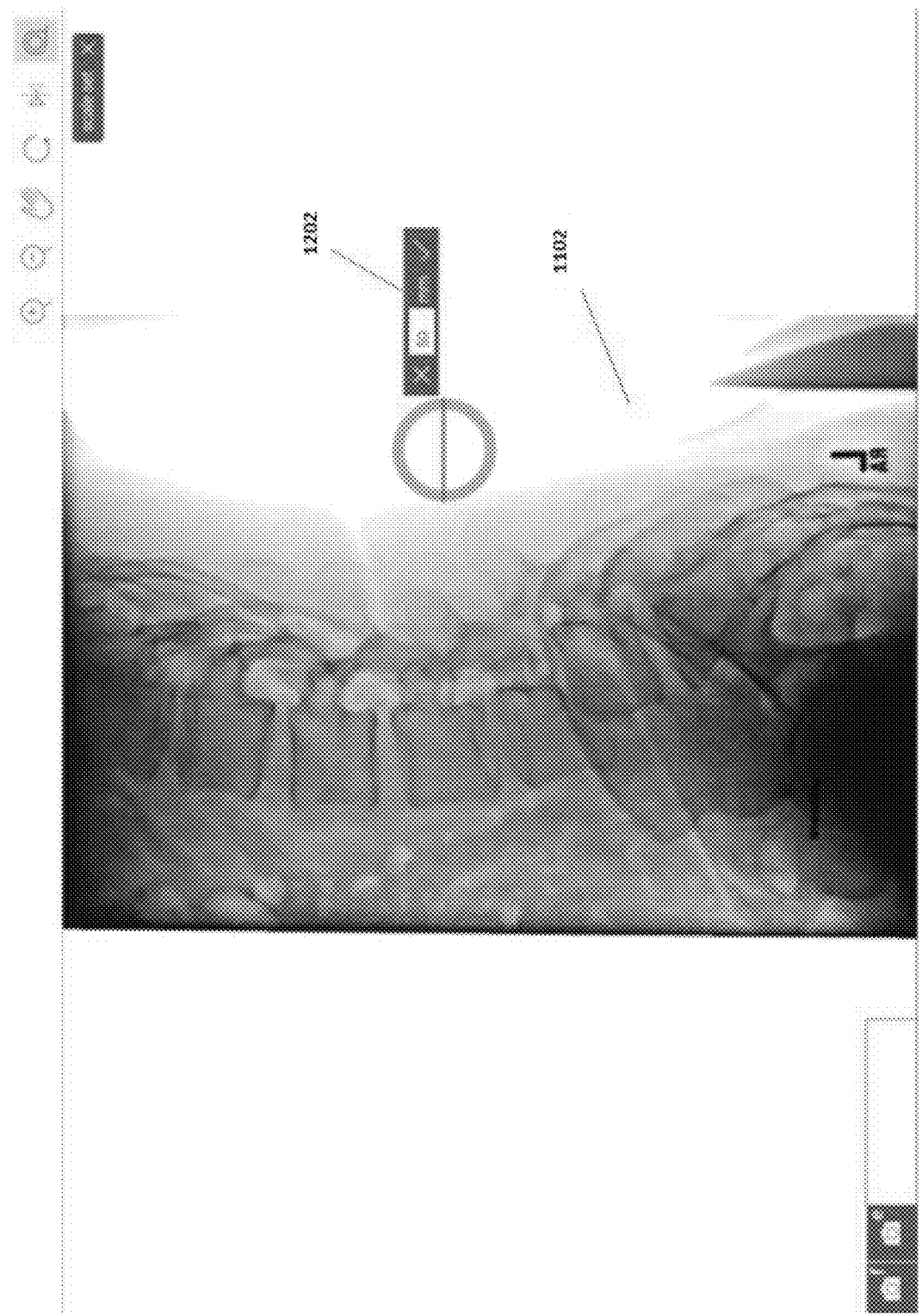

FIGS. 11-12 illustrate example embodiments of a graphical user interface of a system for developing patient-specific medical treatments, operations, and procedures, in which the system is configured to allow analysis of one or more additional images. In particular, FIGS. 11 and 12 illustrate another example of accessing a new drawing layer and/or importing a different image 1102 onto the canvas of the analysis and modeling tool.

In the illustrated embodiment, the image 1102 represents the spinal column of the patient in a neutral or standing state. As with other images described herein, the image 1102 can be displayed with a representation of a steel ball 1104 which was fastened to the body of the patient from which the image 1102 was derived. In the illustrated embodiment, the steel ball 1104 measures 50 mm in diameter and can be used as reference point for setting the drawing scale for the image 1102. In certain embodiments, the user can be permitted to position, zoom, rotate, and/or reflect the image 1102 before proceeding with setting the drawing scale for the image 1102.

In certain embodiments, using the scale tool 1202, the user can draw a line across the known 50 mm length (see FIG. 12) to confirm the proper scale for further modifications or annotations to be made to the image 1102. In some embodiments, due to variance between and among scales of different images, the process of setting the drawing scale may need to be repeated for flexion, extension, and/or neutral or standing positions of the same patient. In certain embodiments, submitting the scale by clicking the appropriate button acts to import the image 1102 onto the canvas of the analysis and modeling tool, which action can be confirmed by displaying a grid on the image 1102 (see FIG. 13).

Figure 13:
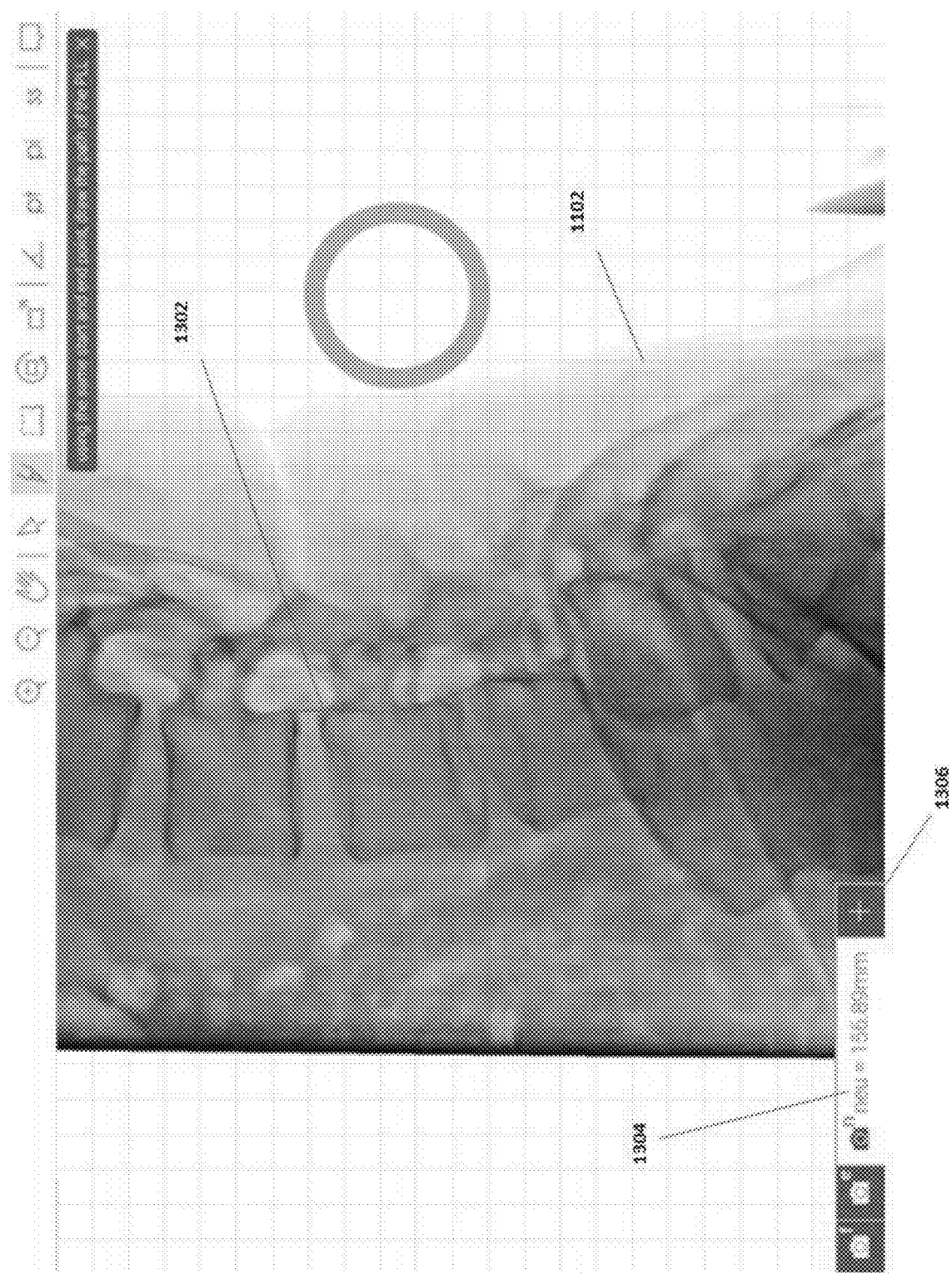
FIG. 13 illustrates an example embodiment of a graphical user interface of a system for developing patient-specific medical treatments, operations, and procedures, in which the graphical user interface comprises a graphical drawing tool.

FIG. 13 illustrates an example embodiment of a graphical user interface of a system for developing patient-specific medical treatments, operations, and procedures, in which the graphical user interface comprises a graphical drawing tool. More specifically, FIG. 13 illustrates an example of drawing a line 1302 along the PLL for the image 1102 using the same or similar start and end points as the flexion image 202 and the extension image 702.

In some embodiments, the user may be prompted to use the same or similar start and end points to promote greater accuracy for the measurement. As shown in FIG. 13, the length of the line 1302 associated with the PLL in its extended position can be displayed in a data field 1304. In certain embodiments, completion of the line 1302 for the image 1102 can result in the analysis and modeling tool generating a link 1306 for generating a new drawing layer. In certain embodiments, once the neutral image 1102 has been imported and its drawing scale set, then additional toolbar controls may be made accessible for modeling the spine.

In certain embodiments, the variance and/or difference among the lengths can be calculated for the flexion line 604, the extension line 902, and/or the neutral line 1302. This variance can be considered the ligament elasticity for the ligament. Values for elasticity can be used by the analysis and modeling tool to determine physical limitations of the ligament, such as for pre-operative planning in advance of adjusting one or more vertebrae during a medical procedure. In some embodiments, the elasticity value may be divided across multiple vertebral spaces positioned between consecutive vertebrae within the spinal column. These calculations can provide an indication of the manner and degree to which vertebrae in a spinal column can be moved, rotated, or otherwise adjusted within the column as described herein.

Figure 14:
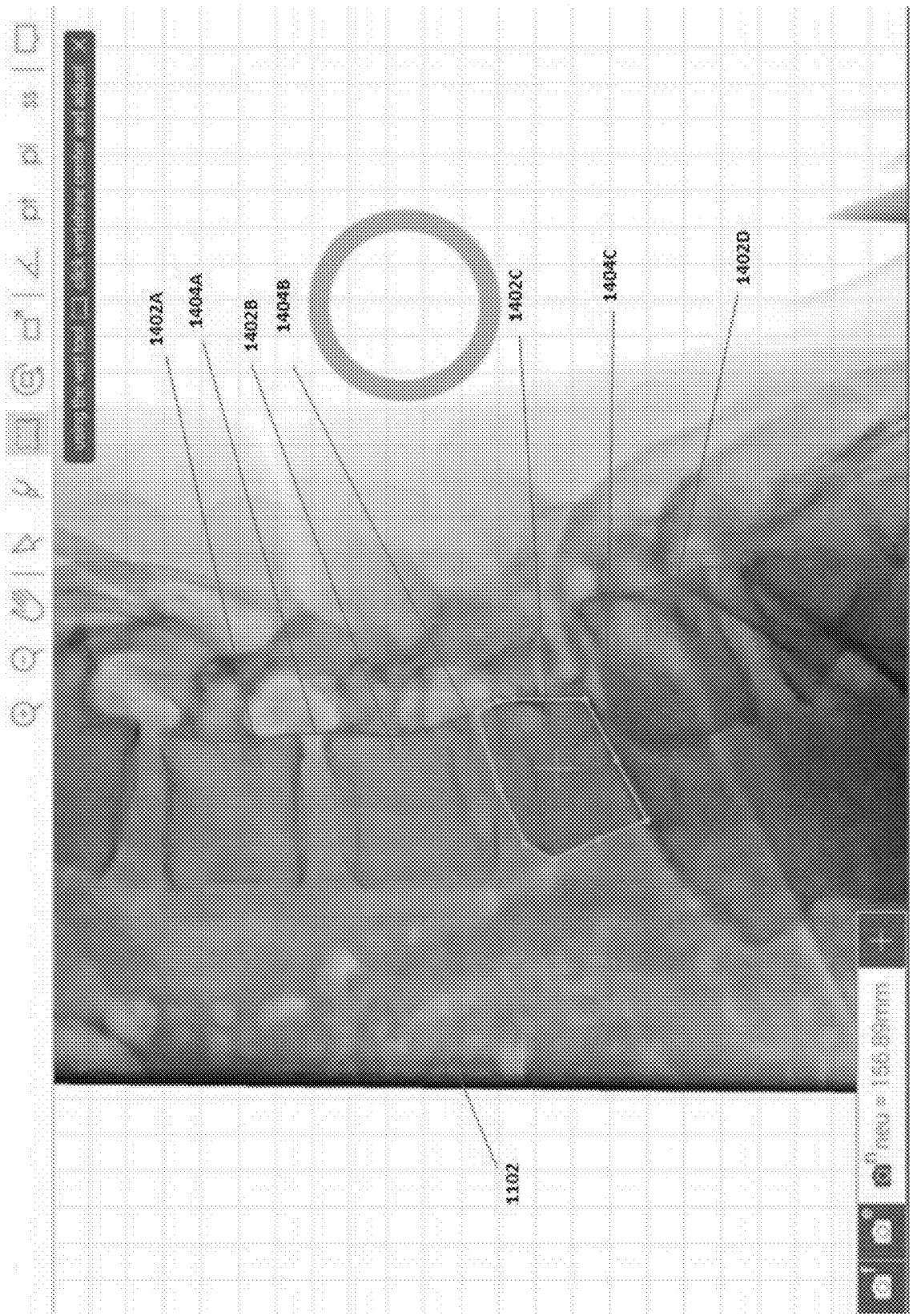
FIGS. 14-15 illustrate example embodiments of a graphical user interface of a system for developing patient-specific medical treatments, operations, and procedures, in which the system is configured to identify one or more features.
Figure 15:
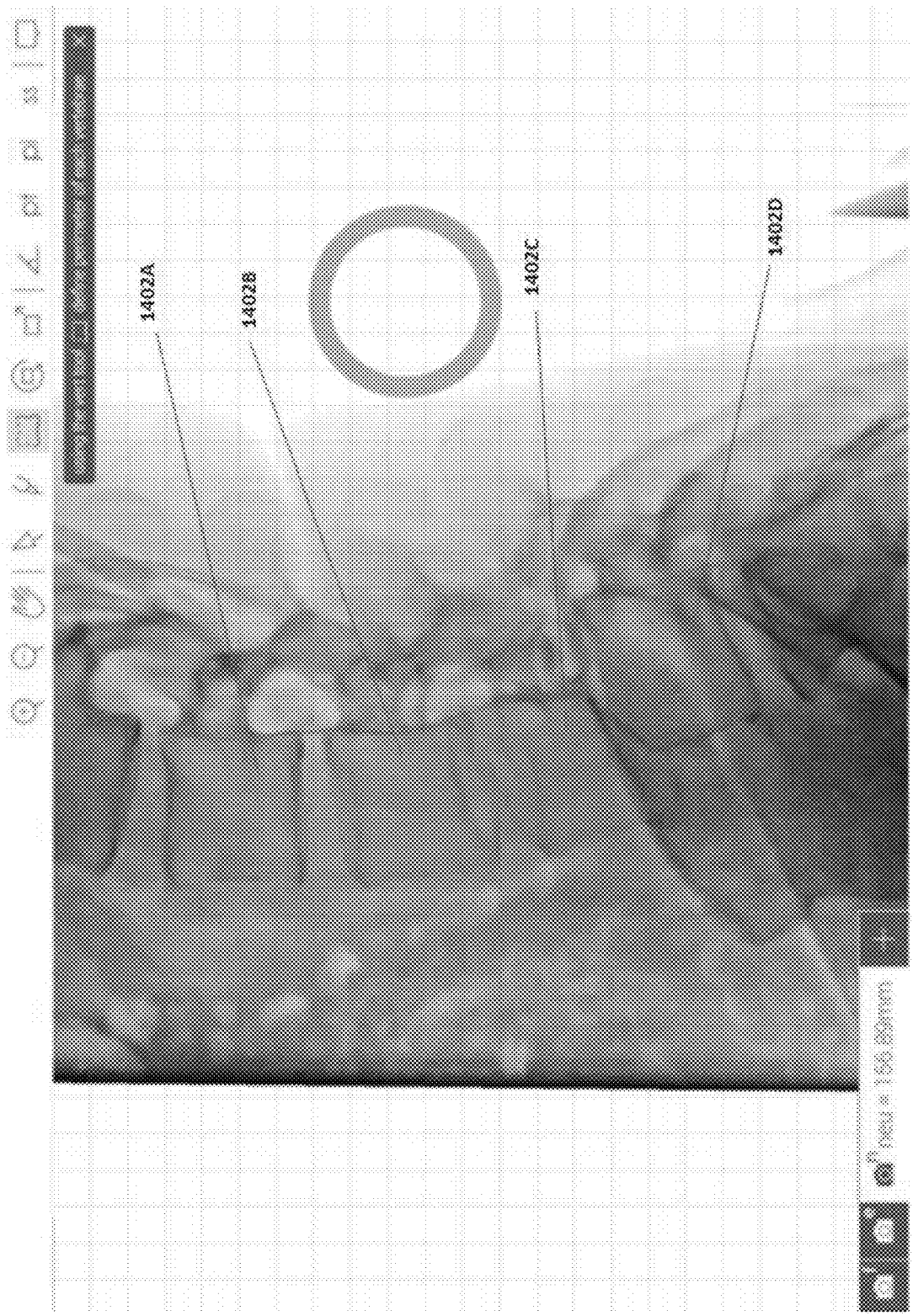

FIGS. 14-15 illustrates example embodiments of a graphical user interface of a system for developing patient-specific medical treatments, operations, and procedures, in which the system is configured to identify one or more features. In particular, with regard to FIGS. 14 and 15, the analysis and modeling tool can be employed to identify or define the boundaries of one or more vertebrae within a spinal column, for example. In certain embodiments, an edge detection algorithm or other suitable image processing algorithm can be applied to the image 1102 to identify multiple vertebrae 1402A-1402D within the spinal column. In certain embodiments, the user can employ the tool to adjust or fine tune the boundaries or borders of each identified vertebra 1402A-1402D. As shown, multiple vertebral spaces 1404A-1404C can be formed between each of the identified vertebrae 1402A-1402D. As described above, a calculated elasticity value may be divided across the vertebral spaces 1404A-1404C to provide an indication of how much the vertebrae 1402A-1402D can be adjusted within the physical limitations of the PLL.

FIGS. 16-18B illustrate example embodiments of a graphical user interface of a system for developing patient-specific medical treatments, operations, and procedures, in which the graphical user interface comprises a feature modification tool. More specifically, FIGS. 16-18B illustrate example embodiments in which the identified vertebrae 1402A-1402D can be moved or adjusted using the analysis and modeling tool.

Figure 16:
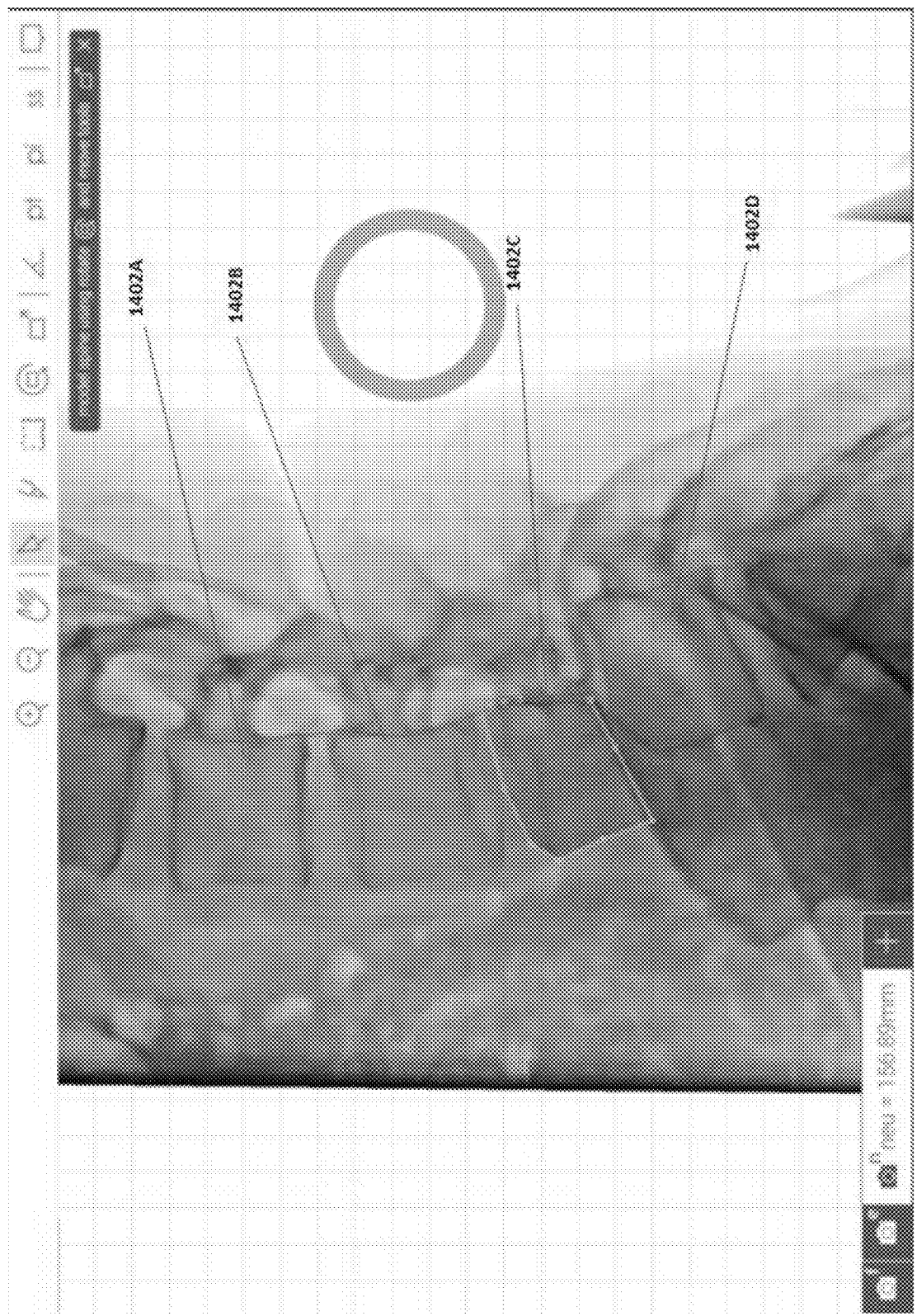
FIGS. 16-18B illustrate example embodiments of a graphical user interface of a system for developing patient-specific medical treatments, operations, and procedures, in which the graphical user interface comprises a feature modification tool.
Figure 17:
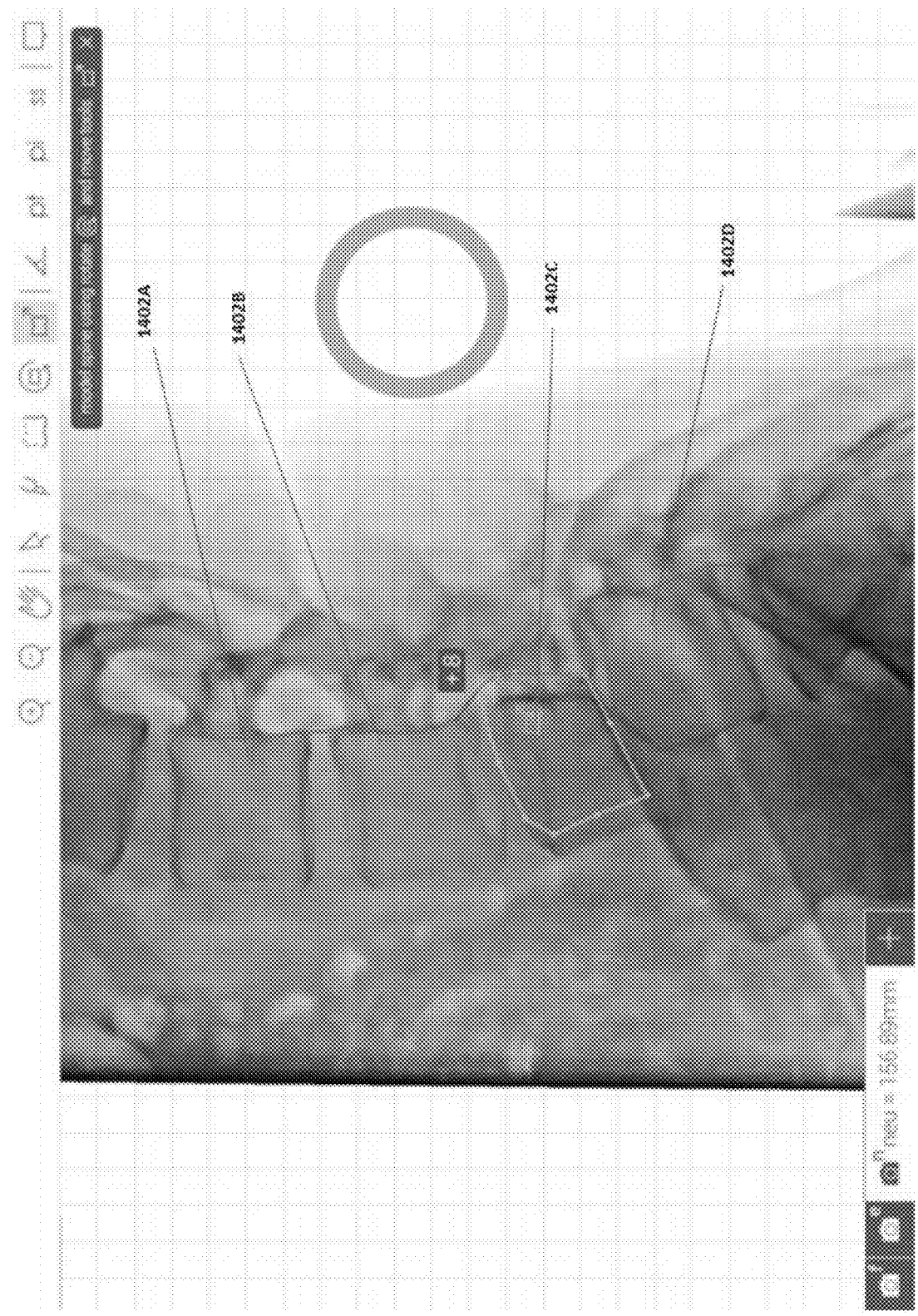
Figure 18A:

FIG. 16 shows an example embodiment of using a select tool to select one 1402C of the vertebrae as a candidate for adjustment or movement. FIG. 17 displays an example embodiment of using a move tool to move the vertebra 1402C. In this example, the PLL is shown adapting to an increase in its length occasioned by the movement, and this increase in length is shown in the display "+.8" graphic. In certain embodiments, the analysis and modeling tool can constrain movement of the vertebrae 1402A-1402D to less than the maximum elasticity calculated. FIG. 18 displays an example embodiment of using a rotate tool to move the vertebra 1402C around a nomination or pivot point. In this example, the PLL is shown adapting to an increase in its length occasioned by the movement, and this increase in length is shown in the display "+1.0" graphic. In certain embodiments, the analysis and modeling tool can constrain rotation of the vertebrae 1402A-1402D to less than the maximum elasticity calculated by the modeling tool.

Figure 18B:
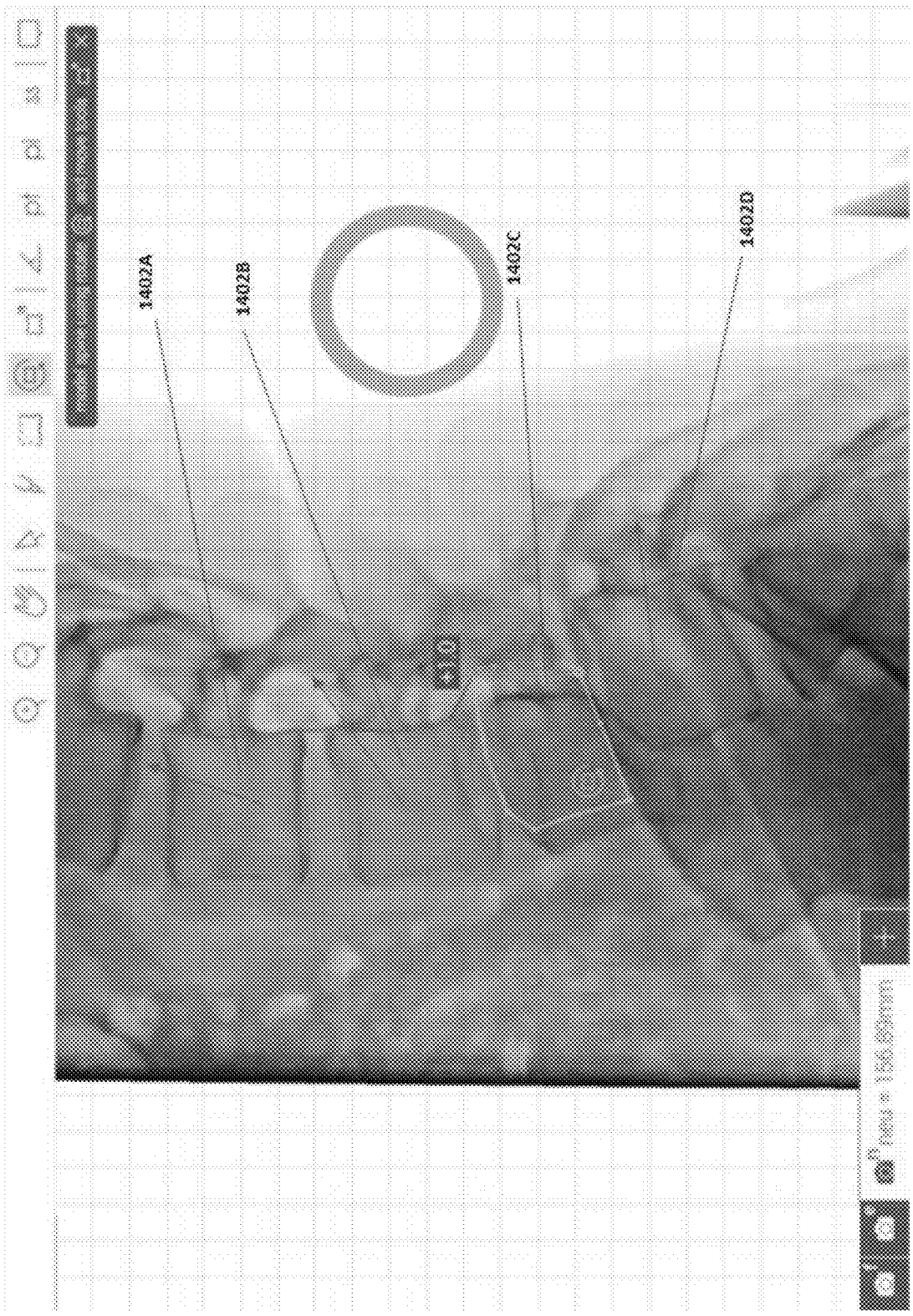

FIG. 18B demonstrates how one or more of the other vertebrae 1402A, 1402B, 1402D may be moved automatically by the analysis and modeling tool in response to movement of the first selected vertebra 1402C. For example, if movement or adjustment of the vertebra 1402C would exceed a predetermined or calculated threshold elasticity level, then one or more of the other vertebrae 1402A, 1402B, 1402D may be correspondingly moved to account for the amount by which the maximum elasticity level has been exceeded. In certain embodiments, the amount by which the maximum elasticity level has been exceeded may be addressed by moving a single vertebra 1402A, 1402B, 1402D. In other embodiments, the amount by which the maximum elasticity level has been exceeded may be addressed by moving a combination of two or more of the other vertebrae 1402A, 1402B, 1402D. In the example shown in FIG. 18B, the directional arrows represent movement by all three of the other vertebrae 1402A, 1402B, 1402D to account for the amount by which the maximum elasticity level has been exceeded by movement of the selected vertebra 1402C.

In certain embodiments, the values may be displayed in colors such as green for an acceptable vertebral move, rotation, or other adjustment; yellow for a marginal or borderline adjustment; and/or red for a movement or adjustment which exceeds a predetermined threshold value. In some embodiments, the system can be configured generate an audio and/or visual alert or warning when a move, rotation, or other adjustment of a vertebra is close to and/or exceeds the maximum elasticity level and/or other predetermined threshold.

Figure 19:
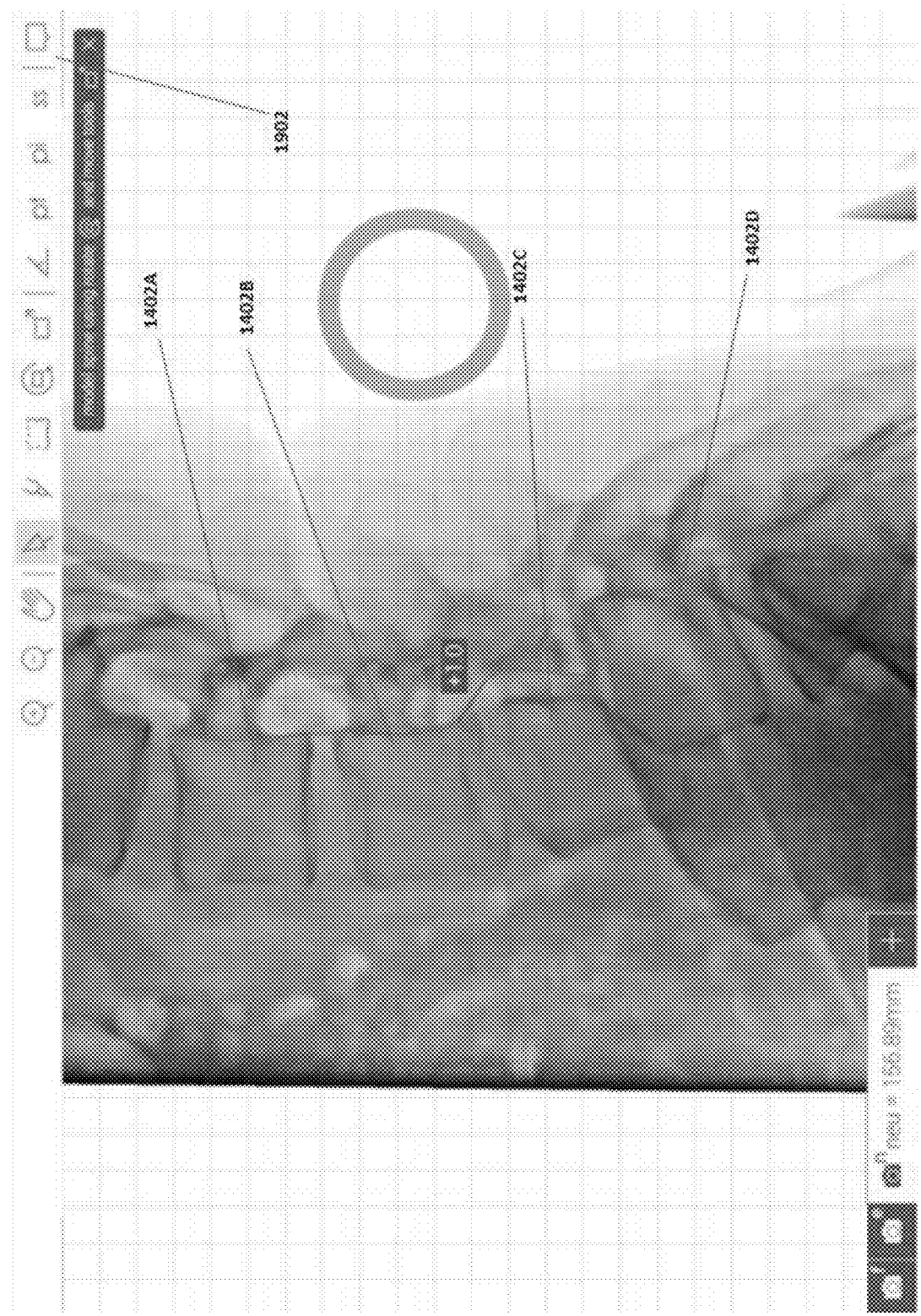
FIG. 19 illustrates an example embodiment of a graphical user interface of a system for developing patient-specific medical treatments, operations, and procedures, in which the graphical user interface comprises a feature modification preview tool.

FIG. 19 illustrates an example embodiment of a graphical user interface of a system for developing patient-specific medical treatments, operations, and procedures, in which the graphical user interface comprises a feature modification preview tool. In particular, FIG. 19 shows an example embodiment of the results of the final positioning of the various vertebrae 1402A-1402D and the PLL within the spinal column. In the illustrated embodiment, after the elements are deselected within the image, the net change in the length of the PLL results in a 1.0 mm increase. Also, in various screen displays provided herein, a comment function 1902 can be provided for adding annotations to each image, such as text comments.

FIGS. 20-23 illustrate example embodiments of a graphical user interface of a system for developing patient-specific medical treatments, operations, and procedures, in which the system is configured to allow access to one or more additional drawing layers. In particular, FIGS. 20-23 illustrate various example embodiments of providing access to multiple drawing layers to facilitate taking measurements and/or for comparing different states of bone or tissue, such as pre-operative and post-operative spinal conditions.

Figure 20:
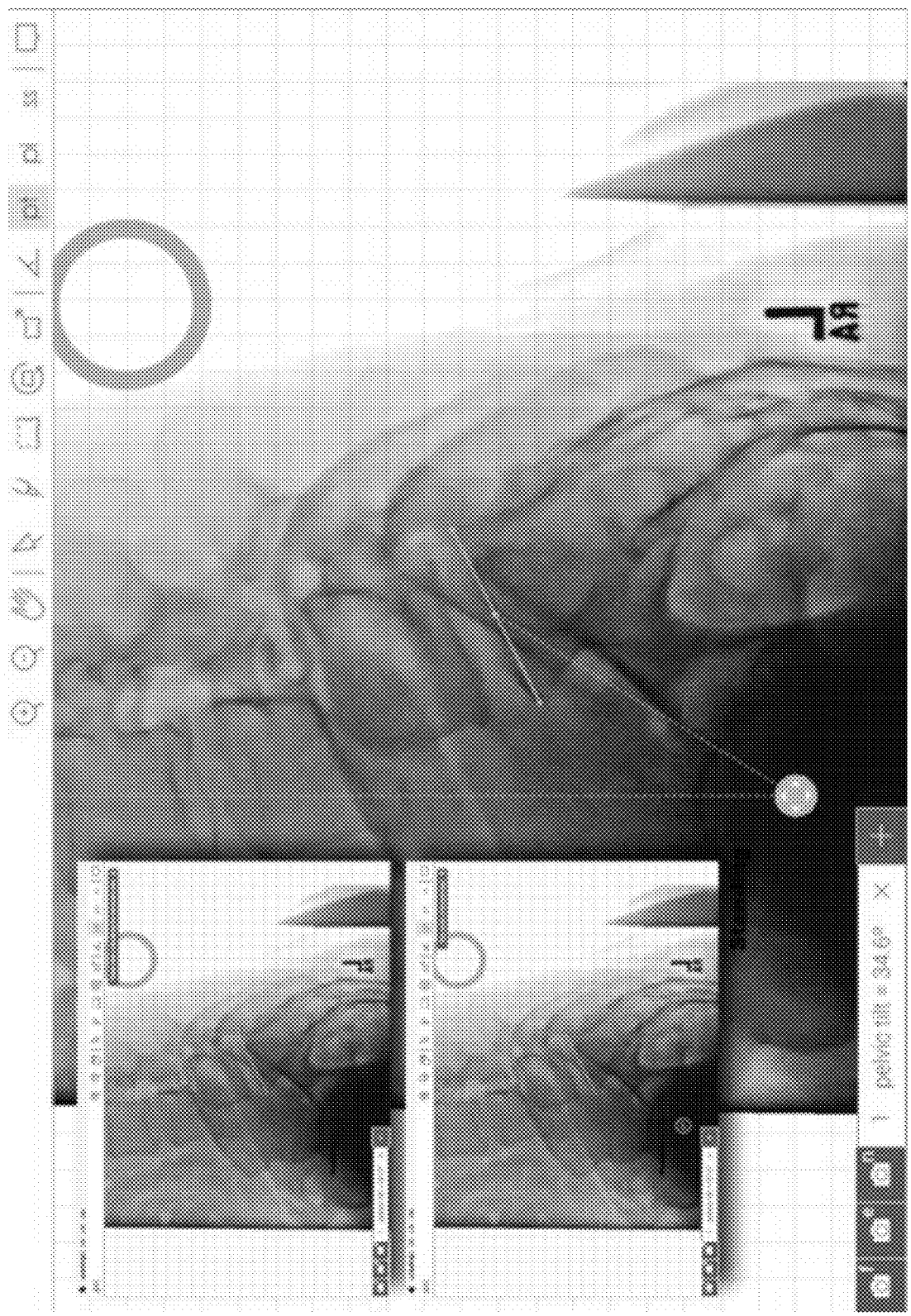
FIGS. 20-23 illustrate example embodiments of a graphical user interface of a system for developing patient-specific medical treatments, operations, and procedures, in which the system is configured to allow access to one or more additional drawing layers.
Figure 21:
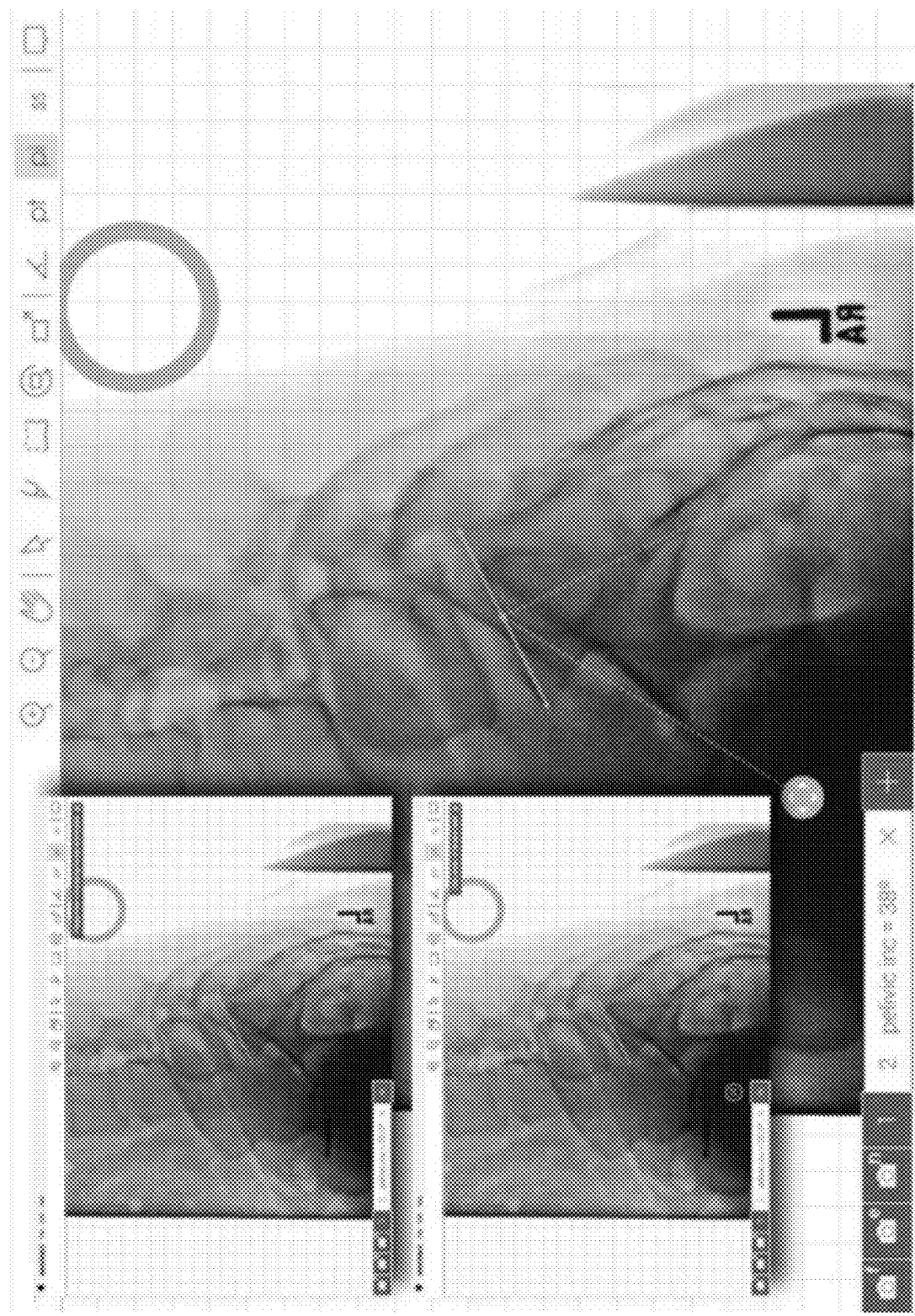
Figure 22:
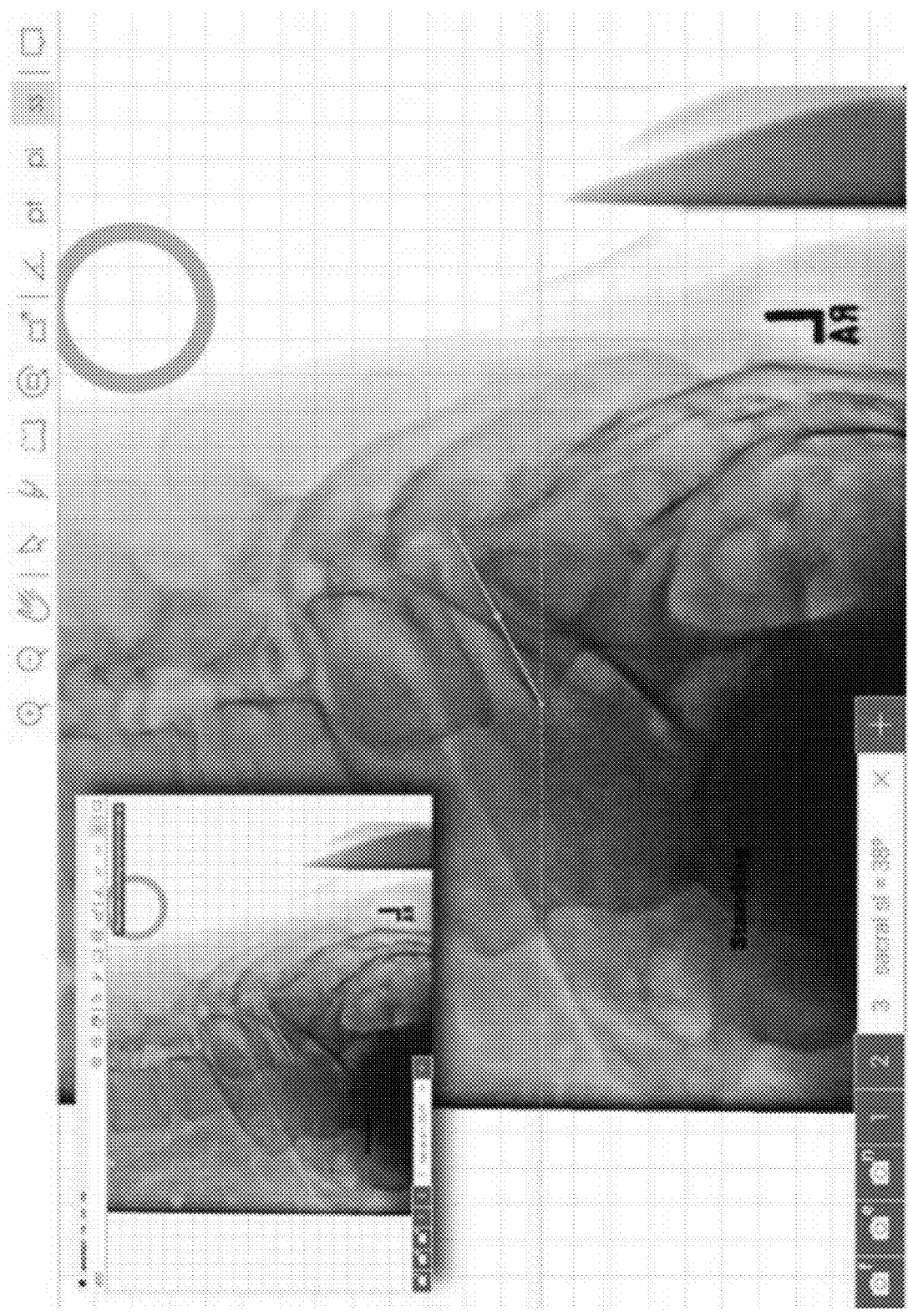

FIG. 20 displays an example embodiment of calculating pelvic tilt by drawing a line along the sacral end plate and then nominating the center of the femoral head. FIG. 21 shows an example embodiment of calculating pelvic incidence by drawing a line along the sacral end plate and then nominating the center of the femoral head. FIG. 22 includes an example embodiment of calculating sacral slope by drawing a line along the sacral end plate.

Figure 23:
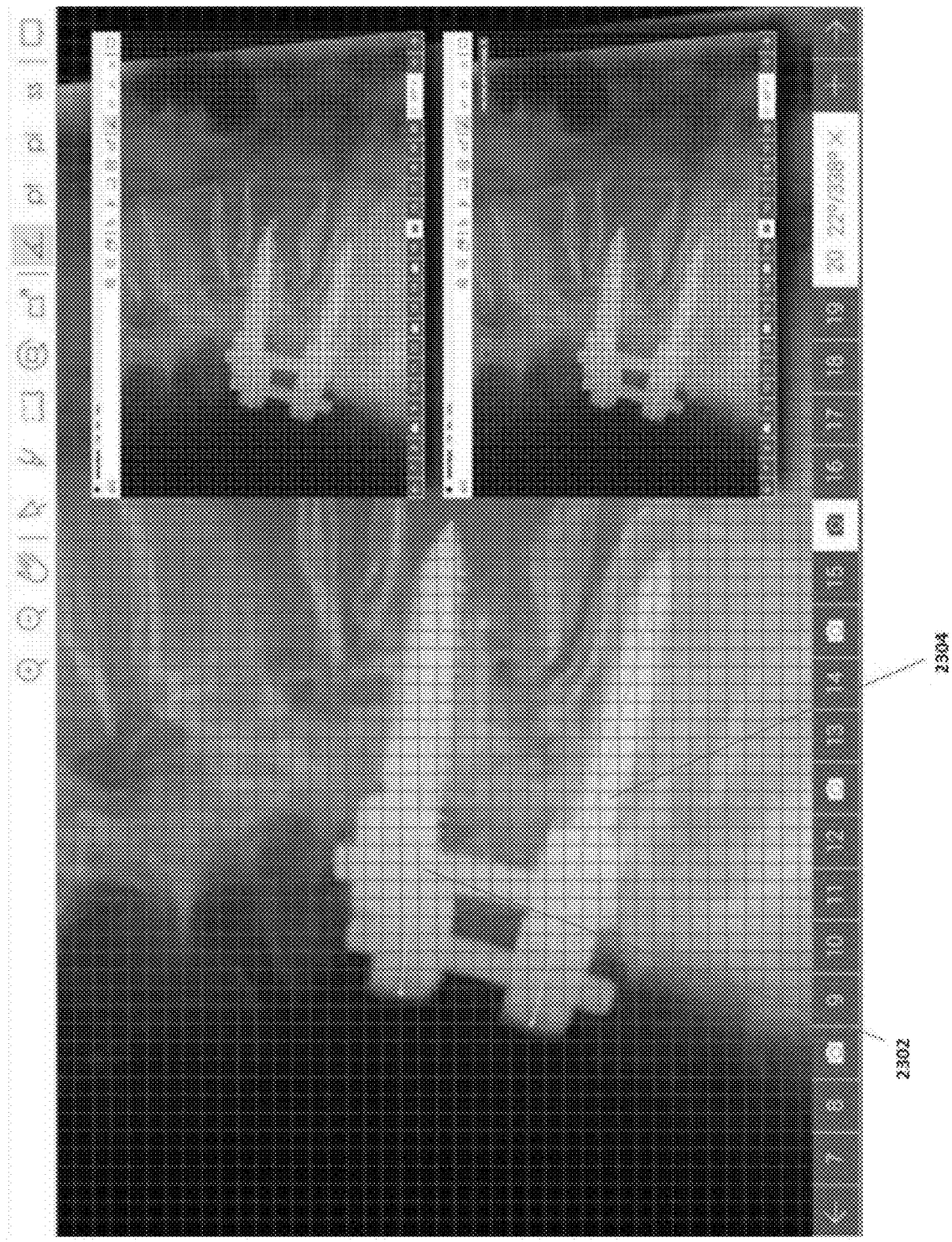

FIG. 23 illustrates an example embodiment of calculating angles for an image by drawing a first arm 2302 and then a second arm 2304. In some embodiments, the analysis and modeling tool can be programmed to calculate the angle without nominating a vertex for the two arms 2302, 2304. As shown, in certain embodiments, one or more layer navigation controls can be programmed to appear when maximum horizontal space is occupied on the screen. Additional images (e.g., displayed as camera icons) can be added from a file menu, for example. In certain embodiments, drawing layers to the right of an image (e.g., 16, 17, 18, 19, 20) can be configured to display different aspects of that selected image.

Integration of Pre-Operative Spinal Radiography and Magnetic Resonance Imaging

As described herein, in some embodiments, one or more medical images, such as x-ray, CT, MRI, or the like, can be used for analysis and/or modeling. In particular, in some embodiments, MRI images and/or techniques can be used to visualize the PLL and/or measure the middle column of a spine. As used herein, the term "middle column" can refer to a region running along the Y-axis of the spine and extending along the Z-axis that is bounded on one side by the posterior surface of each vertebral body in an area near the posterior longitudinal ligaments (PLL), and is bounded on another side (measured along the Z-axis) by a distance substantially one-third of the distance through the vertebral body measured from the posterior surface of the vertebral body in the Z-axis, i.e., from the posterior side to the anterior side of each vertebral body. It is to be understood that the anterior boundary of the middle column can be substantially at the one-third distance (33.3 percent), but the anterior boundary may extend up to 50 percent of the distance through the vertebral body measured long the Z-axis, i.e., the middle column may nominally range of from 0 percent to 33.3 percent, but may range up to 50 percent in certain embodiments.

In some embodiments, using one or more features described herein, the distance between adjacent vertebrae at the middle column may be measured prior to, during and/or after surgery by MRI techniques, which may be used in combination with fluoroscopic, X-ray and/or CT techniques. Dots or other markers may be made on MRI and/or fluoroscopic images taken when the vertebrae are undistracted and taken when the vertebrae are distracted. Then the distances between the non-distracted and distracted dots or markers may be compared to determine the amount of movement along the Y-axis of the spine at the middle column. In some embodiments, the system can be configured to measure the amount of subluxation and translation on standing flexion-extension radiographs in the pre-operative state; however, this may not be optimal as the required spinal laminectomy and decompression have not been performed as yet. As such, in certain embodiments, the system can be configured to assess spinal stability after the required decompression of neural elements and by utilizing skeletal fixation points.

In some embodiments, as described herein, the system is configured to provide integration, scaling, rotation, and/or overlay of preoperative radiographs, preoperative magnetic resonance images (for example, due to their superior soft tissue visualization, particularly the posterior disk and posterior longitudinal ligament) to develop an ideal template. In certain embodiments, such comparison can be displayed and/or compared on a tablet or other user device with an intraoperative fluoroscopic image during surgery of the patient on the operating table. The images can be compared and measured in such a way that a feedback loop can be created to determine whether further decompression, angular osteotomies or larger anterior and middle column spacers should be added intraoperatively.

In certain embodiments, a comparison can be made between preoperative middle column length and middle column length intraoperative after translating or distraction the spine, as disclosed in U.S. patent application Ser. No. 15/344,320 entitled "Methods and Apparatus for Spinal Reconstructive Surgery and Measuring Spinal Length and Intervertebral Spacing, Tension and Rotation," which is incorporated herein by reference. During performance of a spinal surgical procedure, one or more MRI techniques may be used to perform the various disclosed measurements. An instrument may be utilized by the surgeon to determine the optimal spinal height and sagittal and coronal balance.

In certain embodiments, as described herein, one or more software overlays and digital drawing techniques, can be used to apply to spinal imaging to provide custom-made, personalized, unique to each individual patient a 3-D printed cage or fabricated spinal implant.

Figures 24A, 24B:
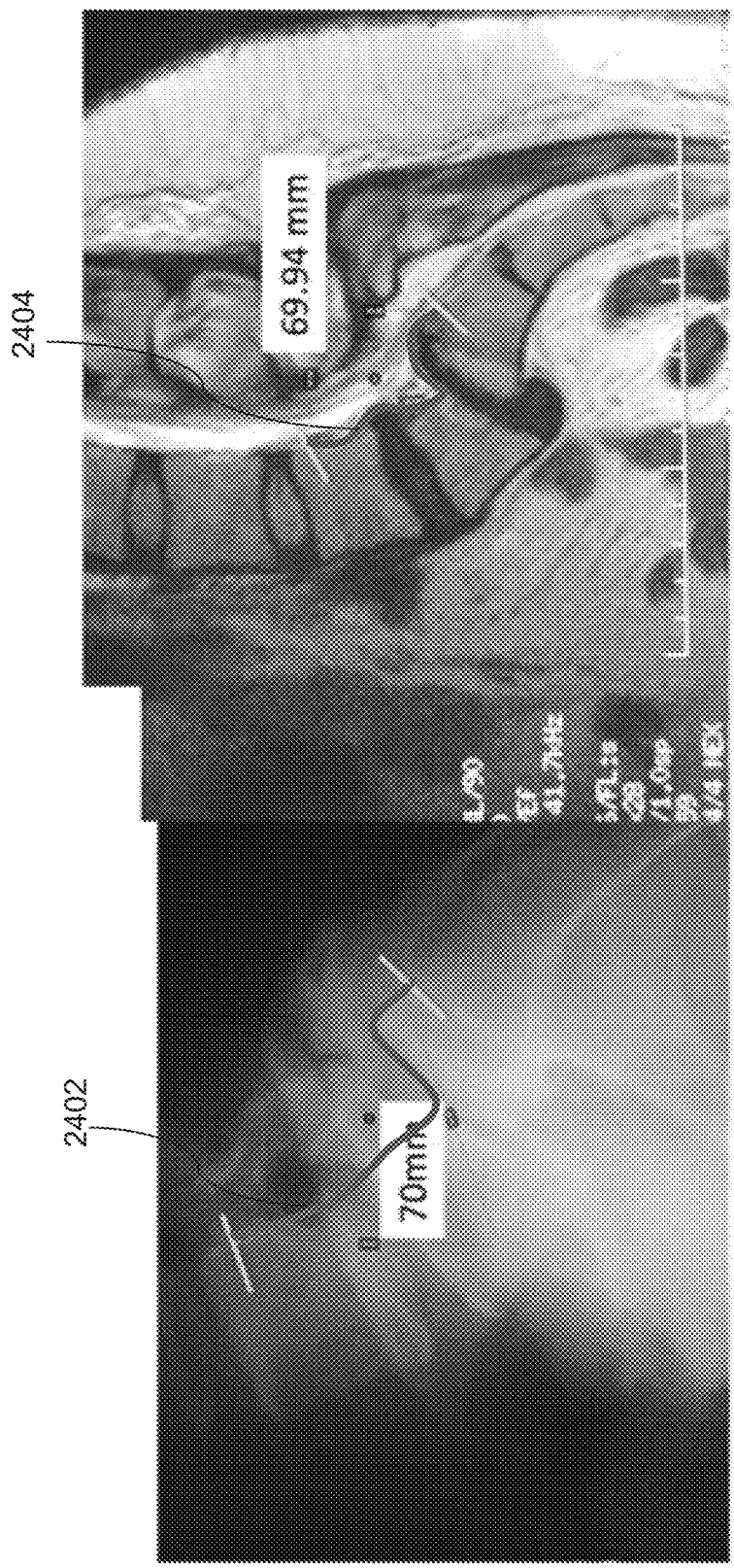
FIG. 24A illustrates an example x-ray image in which a posterior longitudinal ligament (PLL) is transposed using one or more embodiments of the systems, methods, and devices for developing patient-specific medical treatments, operations, and procedures described herein.
FIG. 24B illustrates an example magnetic resonance imaging (MRI) image in which a posterior longitudinal ligament (PLL) is transposed using one or more embodiments of the systems, methods, and devices for developing patient-specific medical treatments, operations, and procedures described herein.

In particular, FIG. 24A illustrates an example x-ray image in which a posterior longitudinal ligament (PLL) is transposed using one or more embodiments of the systems, methods, and devices for developing patient-specific medical treatments, operations, and procedures described herein. Further, FIG. 24B illustrates an example magnetic resonance imaging (MRI) image in which a posterior longitudinal ligament (PLL) is transposed using one or more embodiments of the systems, methods, and devices for developing patient-specific medical treatments, operations, and procedures described herein, for example for accurate middle column measurement. In the illustrated example embodiment of FIG. 24A, a length of the particular portion of PLL of interest can be about 70.0 mm. This measurement can correlate well with the pre-operative MRI measurement, illustrated in FIG. 24B, which can be about 69.94 mm. As illustrated, in some embodiments, the system can be configured to provide a middle column measurement on an X-ray image where the projected image of the PLL can appear with a software layering or overlay technique.

In some embodiments, systems, methods, and devices utilizing magnetic resonance imaging (MRI) in the performance of spinal reconstructive surgery can comprise measuring the spinal length in the Y-axis at the middle column, measuring intervertebral spacing in the Y-axis at the middle column, measuring intervertebral tension applied to the posterior longitudinal ligament, establishing the height of intervertebral spacers along the Y-axis at the middle column based on one or more of such measurements, measuring intervertebral rotation around the Y-axis, and measuring flexion-extension or anterior-posterior rotation around the X-axis.

In certain embodiments, measuring spacing length at a middle column of a spine utilizing MRI techniques can comprise positioning a first middle column marker in a first vertebra within the middle column, positioning a second middle column marker in a second vertebra within the middle column, and measuring via MRI techniques a distance between the first and second middle column markers to thereby determine the intervertebral spacing length at the middle column.

In some embodiments, measuring spinal length at a middle column of a spine using MRI techniques can comprise identifying the location of the middle column for individual vertebrae along at least a portion of the length of the spine, measuring the length of each of the vertebrae at the middle column, measuring intervertebral lateral offset distances between adjacent vertebrae, and determining an overall spinal length representing a combination of the measured lengths of the vertebrae at the middle column and the measured intervertebral lateral offset distances.

In certain embodiments, measuring intervertebral tension of a spine utilizing MRI techniques can comprise positioning a first bone anchor in a first vertebra within a middle column of the spine, positioning a second bone anchor in a second vertebra within the middle column of the spine, distracting the first and second vertebrae by applying force against the first and second bone anchors, and measuring tension of a posterior longitudinal ligament between the first and second vertebrae at different distraction distances.

In some embodiments, a method of spinal reconstructive surgery can comprise measuring via MRI techniques a pre-operative spinal length at a middle column of the spine, and establishing at least one intervertebral spacing in the spine based on the measured pre-operative spinal length at the middle column.

In certain embodiments, a method for measuring rotational displacement of adjacent vertebrae of a spine via MRI techniques can comprise positioning a middle column marker in at least two vertebrae of the spine within a middle column of the spine, applying a force between the middle column markers, and measuring relative angular movement between the middle column markers.

In some embodiments, an apparatus for measuring intervertebral spacing distances between adjacent vertebrae at a middle column of a spine via MRI techniques can comprise at least two middle column markers positionable in at least two vertebrae within a middle column of the spine, and a detector capable of measuring a distance between the middle column markers at the middle column.

In certain embodiments, systems, methods, and devices described herein can provide a real-time and/or near real-time measurement guide. In particular, tensioning may be done as maneuvers are performed reducing the spine. In some embodiments, integrated real-time or near real-time two-dimensional and/or three-dimensional mapping may be provided in accordance. To do so, in certain embodiments, MRI techniques may be used alone, or in combination with one or more fluoroscopy, X-ray or TC techniques. The middle column measurements may be measured pre-operatively, intraoperatively and/or postoperatively.

In some embodiments, the system can allow a medical professional to measure the actual effect of the cage or spine manipulation on the middle column. Actual middle column height can be measured including any changes in middle column height, along with angular changes. The output versus the idealized input may be provided. Certain example computerized mapping programs can measure only the idealized introduction, e.g., of an 11 mm cage even though there is subsidence and it only increases the axial height at the middle column 9.5 mm. Subsidence can be common as the vertebral bodies can be osteoporotic and the cage might sink into the softer bone to some extent. In certain procedures, a 30 degree hyperlordotic cage may yield a correction of 8.5 to 41.1 degrees, which may be an unacceptably wide variation and too unpredictable. Certain systems may only measure the idealized angles and do not measure the tension or the actual axial spinal height. Variation or unpredictability may result from subsidence, inadequate soft tissue release and lack of PLL tension measurement.

As such, certain embodiments of the systems, devices, and methods herein can provide precise measurements at the middle column, thereby giving surgeons better guidance. In some embodiments, precise measurements may be integrated into an automated or robotic system. Ligament tension (i.e., PLL) may be used as a gauge for 3D spinal re-alignment/global spinal balance. In certain embodiments, an MC measurement gauge may be used to ensure that vertebral bone and cage height match up with PLL tension. In some embodiments, benefits can increase across multiple levels because small errors can otherwise be compounded across multiple levels. Problems from over/under distraction can include: in cervical-chin on chest deformity; in lumbar-flat back syndrome; improper anterior load sharing; and pedicle screw breakage/cage dislodgement/pseudarthrosis. Certain embodiments of systems, methods, and devices herein can make spinal surgical and/or treatment results more reproducible and predictable.

Patient-Specific Implants

FIG. 25A-C illustrate example implants that can be designed and/or selected for a particular patient using one or more embodiments of the systems, methods, and devices for developing patient-specific medical treatments, operations, and procedures described herein. In some embodiments, based on one or more medical image analyses and/or modifications, the system can be configured to generate instructions and/or features of one or more patient-specific implants.

For example, in some embodiments, the system can be configured to specify one or more features of a patient-specific spinal rod for implantation, such as the one illustrated in FIG. 25B, which may comprise the diameter, length, and/or curvature of the spinal rod. Similarly, in certain embodiments, the system can be configured to specify one or more features of a patient-specific cages or intervertebral spacers for implantation, such as the one illustrated in FIG. 25A, which may comprise the height, length, thickness, and/or other dimension(s) of the cage or intervertebral spacer. In addition, in some embodiments, the system can be configured to specify one or more features of patient-specific screws for implantation, such as the one illustrated in FIG. 25C, which may comprise the height, length, thickness, shape, and/or other dimension(s) or feature of the screw. Further, in some embodiments, the system can be able to recommend that one or more particular screws, rods, intervertebral spacers, and/or cages be included in a surgical kit and/or treatment kit for a particular patient. Based on such patient-implant specifications as determined by and/or using one or more embodiments herein, an implant generation and/or selection system can be configured to produce, put together, and/or otherwise deliver one or more patient-specific implants.

Figure 26:
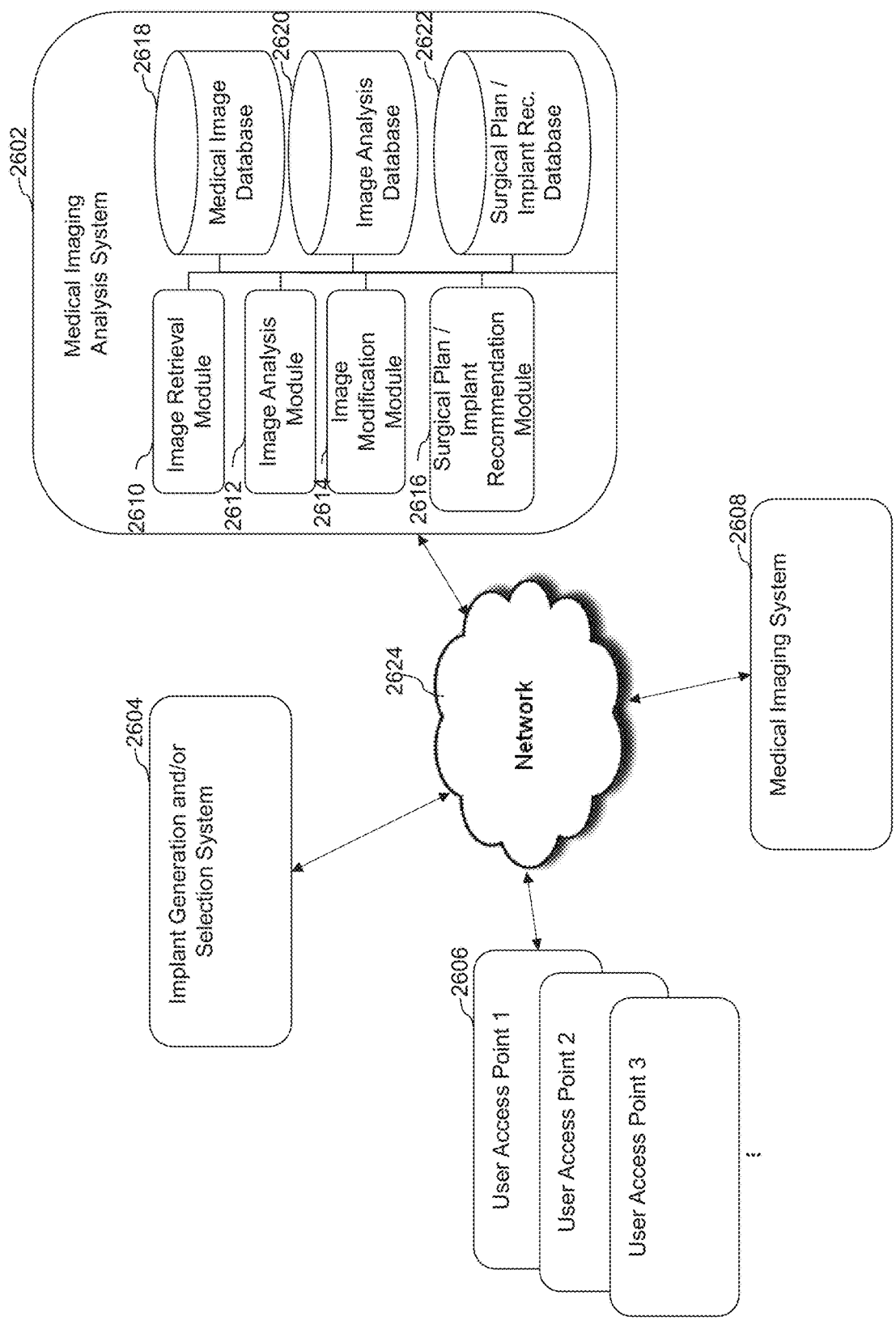
FIG. 26 is a schematic diagram illustrating one or more embodiments of a system for developing patient-specific medical treatments, operations, and procedures.

System(s) for Developing Patient-Specific Medical Treatments, Operations, and Procedures FIG. 26 is a schematic diagram illustrating an embodiment of a system for developing patient-specific spinal treatments, operations, and procedures. In some embodiments, a medical imaging analysis system 2602 may comprise an image retrieval module 2610, an image analysis module 2612, an image modification module 2614, a surgical plan/implant recommendation module 2616, a medical image database 2618, an image analysis database 2620, and/or a surgical plan/implant recommendation database 2622. The medical imaging analysis system 2602 can be connected to a network 2624. The network 2624 can be configured to connect the medical imaging analysis system 2602 to one or more implant generation and/or selection systems 2604, one or more medical imaging systems 2608, and/or one or more user access point systems 2606.

The image retrieval module 2610 may function by retrieving medical images and/or related functions as described herein. The image analysis module 2612 may function by providing image analysis and/or related functions as described herein. The image modification module 2614 may function by modifying and/or allowing modification of features of medical images and/or related functions as described herein. The surgical plan/implant recommendation module 2616 may function by recommending surgical plans and/or implants and/or related functions as described herein.

The medical image database 2618 may provide a collection of all or some medical images that have been collected and/or retrieved and/or related data. The image analysis database 2620 may provide a collection of all or some analytical results, tools, and/or framework and/or related data. The surgical plan/implant recommendation database 2622 may provide a collection of all or some surgical plans and/or implant recommendations and/or related data.

Computer System

Figure 27:
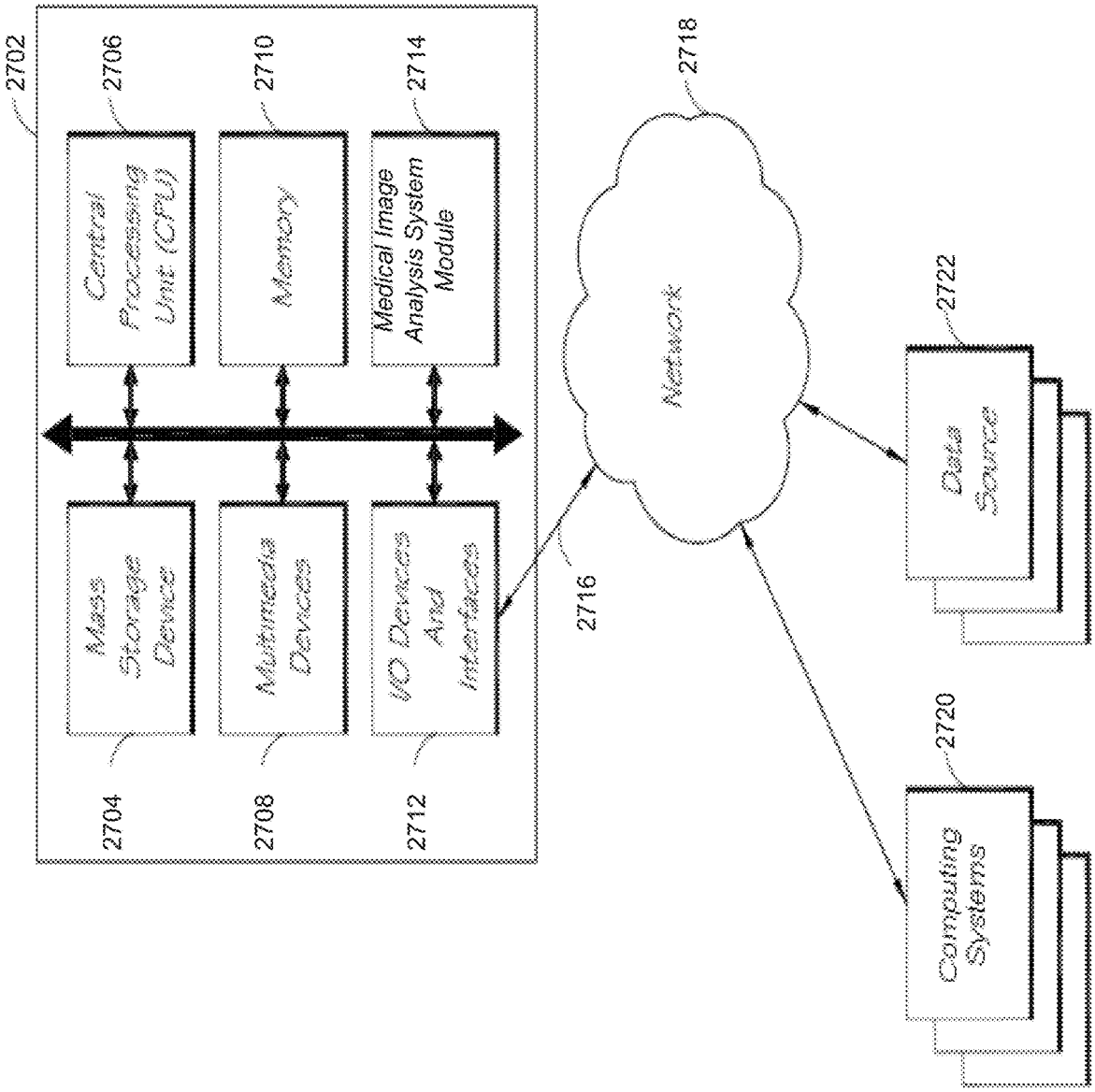
FIG. 27 is a schematic diagram illustrating an embodiment of a computer hardware system configured to run software for implementing one or more embodiments of methods for developing patient-specific medical treatments, operations, and procedures.

In some embodiments, the systems, devices, and methods described herein are implemented using a computing system, such as the one illustrated in FIG. 27. FIG. 27 is a schematic diagram illustrating an embodiment of a computer hardware system configured to run software for implementing one or more embodiments of methods for developing patient-specific medical treatments, operations, and procedures. While FIG. 27 illustrates one embodiment of a computing system 2702, it is recognized that the functionality provided for in the components and modules of computing system 2702 may be combined into fewer components and modules or further separated into additional components and modules.

Medical Image Analysis System Module

In some embodiments, the computing system 2702 comprises a medical image analysis system module 2714 that carries out the functions described herein, including any one of techniques described above. The medical image analysis system module 2714 and/or other modules may be executed on the computing system 2702 by a central processing unit 2706 discussed further below.

In general, the word "module," as used herein, refers to logic embodied in hardware or firmware, or to a collection of software instructions, possibly having entry and exit points, written in a programming language, such as, for example, COBOL, CICS, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into submodules despite their physical organization or storage.

Computing System Components

In one embodiment, the computing system 2702 also comprises a mainframe computer suitable for controlling and/or communicating with large databases, performing high volume transaction processing, and generating reports from large databases. The computing system 2702 also comprises a central processing unit ("CPU") 2706, which may comprise a conventional microprocessor. The computing system 2702 further comprises a memory 2710, such as random access memory ("RAM") for temporary storage of information and/or a read only memory ("ROM") for permanent storage of information, and a mass storage device 2704, such as a hard drive, diskette, or optical media storage device. Typically, the modules of the computing system 2702 are connected to the computer using a standards based bus system. In different embodiments, the standards based bus system could be Peripheral Component Interconnect (PCI), Microchannel, SCSI, Industrial Standard Architecture (ISA) and Extended ISA (EISA) architectures, for example.

The computing system 2702 comprises one or more commonly available input/output (I/O) devices and interfaces 2712, such as a keyboard, mouse, touchpad, and printer. In one embodiment, the I/O devices and interfaces 2712 comprise one or more display devices, such as a monitor, that allows the visual presentation of data to a user. More particularly, a display device provides for the presentation of GUIs, application software data, and multimedia presentations, for example. In one or more embodiments, the I/O devices and interfaces 2712 comprise a microphone and/or motion sensor that allow a user to generate input to the computing system 2702 using sounds, voice, motion, gestures, or the like. In the embodiment of FIG. 27, the I/O devices and interfaces 2712 also provide a communications interface to various external devices. The computing system 2702 may also comprise one or more multimedia devices 2708, such as speakers, video cards, graphics accelerators, and microphones, for example.

Computing System Device/Operating System

The computing system 2702 may run on a variety of computing devices, such as, for example, a server, a Windows server, a Structure Query Language server, a Unix server, a personal computer, a mainframe computer, a laptop computer, a tablet computer, a cell phone, a smartphone, a personal digital assistant, a kiosk, an audio player, an e-reader device, and so forth. The computing system 2702 is generally controlled and coordinated by operating system software, such as z/OS, Windows 95, Windows 98, Windows NT, Windows 2000, Windows XP, Windows Vista, Windows 7, Windows 8, Linux, BSD, SunOS, Solaris, Android, iOS, BlackBerry OS, or other compatible operating systems. In Macintosh systems, the operating system may be any available operating system, such as MAC OS X. In other embodiments, the computing system 2702 may be controlled by a proprietary operating system. Conventional operating systems control and schedule computer processes for execution, perform memory management, provide file system, networking, and I/O services, and provide a user interface, such as a graphical user interface ("GUI"), among other things.

Network

In the embodiment of FIG. 27, the computing system 2702 is coupled to a network 2718, such as a LAN, WAN, or the Internet, for example, via a wired, wireless, or combination of wired and wireless, communication link 2716. The network 2718 communicates with various computing devices and/or other electronic devices via wired or wireless communication links. In the embodiment of FIG. 27, the network 2718 is communicating with one or more computing systems 2720 and/or one or more data sources 2722.

Access to the medical image analysis system module 2714 of the computer system 2702 by computing systems 2720 and/or by data sources 2722 may be through a web-enabled user access point such as the computing systems' 2720 or data source's 2722 personal computer, cellular phone, smartphone, laptop, tablet computer, e-reader device, audio player, or other device capable of connecting to the network 2718. Such a device may have a browser module that is implemented as a module that uses text, graphics, audio, video, and other media to present data and to allow interaction with data via the network 2718.

The browser module may be implemented as a combination of an all points addressable display such as a cathode-ray tube (CRT), a liquid crystal display (LCD), a plasma display, or other types and/or combinations of displays. In addition, the browser module may be implemented to communicate with input devices 2712 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 2702 may comprise a physical or logical connection established between a remote microprocessor and a mainframe host computer for the express purpose of uploading, downloading, or viewing interactive data and databases on-line in real time. The remote microprocessor may be operated by an entity operating the computer system 2702, including the client server systems or the main server system, an/or may be operated by one or more of the data sources 2722 and/or one or more of the computing systems 2720. In some embodiments, terminal emulation software may be used on the microprocessor for participating in the micro-mainframe link.

In some embodiments, computing systems 2720 who are internal to an entity operating the computer system 2702 may access the medical image analysis system module 2714 internally as an application or process run by the CPU 2706.

URLs and Cookies

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

Other Systems

In addition to the systems that are illustrated in FIG. 27, the network 2718 may communicate with other data sources or other computing devices. The computing system 2702 may also comprise one or more internal and/or external data sources. In some embodiments, one or more of the data repositories and the data sources may be implemented using a relational database, such as DB2, Sybase, Oracle, CodeBase and Microsoft® SQL Server as well as other types of databases such as, for example, a flat file database, an entity-relationship database, and object-oriented database, and/or a record-based database.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

What is claimed is:

1. A computer-implemented method for producing a patient-specific spinal implant, the method comprising, by a computer system:
    receiving, from a medical imaging system, one or more pre-operative medical images of a spine of a patient in each of a flexion, extension, and neutral posture;
    displaying, on a graphical user interface, at least one image of the patient in each of the postures;
    for each posture:
        receiving, through the graphical user interface, a line drawn by a user, the line representing a path of a posterior longitudinal ligament of the spine; and
        determining a length of the posterior longitudinal ligament of the spine based on the drawn line;
    determining a value for ligament elasticity of the posterior longitudinal ligament based on a variance among the determined lengths of the posterior longitudinal ligament of the spine in each of the flexion, extension, and neutral postures;
    determining a recommended limit of correction of the spine based at least in part on one or more of the determined lengths of the posterior longitudinal ligament and the value for ligament elasticity of the posterior longitudinal ligament;
    receiving through the graphical user interface, user selection of a vertebra from one or more medical images of the spine of the patient;
    receiving, through the graphical user interface, user input representing one or more modifications to the selected vertebra, wherein the one or more modifications comprise at least one or more of displacement or rotation of the selected vertebra;
    dynamically determining whether the one or more modifications to the vertebra is within the determined recommended limit of correction of the spine;
    dynamically updating the one or more pre-operative medical images, based on the user selection of the vertebra and the received one or more modifications to the selected vertebra, upon determination that the one or more modifications to the vertebra is within the determined recommended limit of correction of the spine;
    generating one or more desired post-operative medical images of the spine based at least in part on the dynamically updated one or more pre-operative medical images;
    determining one or more specifications of one or more patient-specific spinal implants for the patient based at least in part on the generated one or more desired post-operative medical images of the spine; and
    transmitting the one or more specifications of the one or more patient-specific spinal implants to a spinal implant production system for producing the one or more patient-specific spinal implants,
    wherein the computer system comprises a computer processor and an electronic storage medium.

2. The method of claim 1, wherein the posterior longitudinal ligament is identified by the user tracing the posterior longitudinal ligament on the one or more pre-operative medical images of the spine.

3. The method of claim 1, further comprising generating an alert, by the computer system, upon determination that the one or more modifications to the vertebra is not within the determined recommended limit of correction of the spine.

4. The method of claim 1, wherein the one or more pre-operative medical images comprises an x-ray image of the spine of the patient in one or more of a flexion, extension, or neutral posture.

5. The method of claim 1, wherein the one or more pre-operative medical images comprises one or more of an x-ray image, a CT image, or an MRI image.

6. The method of claim 1, further comprising scaling the one or more pre-operative medical images.

7. The method of claim 6, wherein the scaling is based at least in part on a reference point or object of the one or more pre-operative medical images.

8. The method of claim 1, wherein the one or more patient-specific spinal implants comprises one or more of a spinal rod, intervertebral spacer, cage, or screw for use in spinal surgery.

9. A system for producing a patient-specific spinal implant, the system comprising:
    one or more computer readable storage devices configured to store a plurality of computer executable instructions; and one or more hardware computer processors in communication with the one or more computer readable storage devices and configured to execute the plurality of computer executable instructions in order to cause the system to:

receive one or more pre-operative medical images of a spine of a patient in each of a flexion, extension, and neutral posture;

display, on a graphical user interface, at least one image of the patient in each of the postures;

for each posture:

receive, through the graphical user interface, a line drawn by a user, the line representing a path of a posterior longitudinal ligament of the spine; and determine a length of the posterior longitudinal ligament of the spine based on the drawn line;

determine a value for ligament elasticity of the posterior longitudinal ligament based on a variance among the determined lengths;

determine a recommended limit of correction of the spine based at least in part on one or more of the determined lengths of the posterior longitudinal ligament and the value for ligament elasticity of the posterior longitudinal ligament;

receive, through the graphical user interface, user selection of a vertebra from one or more medical images of the spine of the patient;

receive, through the graphical user interface, user input representing one or more modifications to the selected vertebra, wherein the one or more modifications comprise at least one or more of displacement or rotation of the selected vertebra;

dynamically determine whether the one or more modifications to the vertebra is within the determined recommended limit of correction of the spine;

dynamically update the one or more pre-operative medical images, based on the user selection of the vertebra and the received one or more modifications to the selected vertebra, upon determination that the one or more modifications to the vertebra is within the determined recommended limit of correction of the spine;

generate one or more desired post-operative medical images of the spine based at least in part on the dynamically updated one or more pre-operative medical images;

determine one or more specifications of one or more patient-specific spinal implants for the patient based at least in part on the generated one or more desired post-operative medical images of the spine; and transmit the one or more specifications of the one or more patient-specific spinal implants to a spinal implant production system for producing the one or more patient-specific spinal implants.

10. The system of claim 9, wherein the posterior longitudinal ligament is identified by the system based at least in part on user input, wherein the user input comprises tracing the posterior longitudinal ligament on the one or more pre-operative medical images of the spine.

11. The system of claim 9, wherein the system is further caused to generate an alert upon determination that the one or more modifications to the vertebra is not within the determined recommended limit of correction of the spine.

12. The system of claim 9, wherein the one or more pre-operative medical images comprises an x-ray image of the spine of the patient in one or more of a flexion, extension, or neutral posture.

13. The system of claim 9, wherein the one or more pre-operative medical images comprises one or more of an x-ray image, a CT image, or an MRI image.

14. The system of claim 9, wherein the system is further caused to scale the one or more pre-operative medical images.

15. The system of claim 14, wherein the scaling is based at least in part on a reference point or object of the one or more pre-operative medical images.

16. The system of claim 9, wherein the one or more patient-specific spinal implants comprises one or more of a spinal rod, intervertebral spacer, cage, or screw for use in spinal surgery.

* * * * *